US005824867A

United States Patent [19]
Coruzzi et al.

[11] Patent Number: 5,824,867
[45] Date of Patent: Oct. 20, 1998

[54] PLANT GLUTAMATE RECEPTORS

[75] Inventors: Gloria Coruzzi; Igor Oliveira; Hon-Ming Lam, all of New York; Ming-Hsiun Hsieh, Woodside, all of N.Y.

[73] Assignee: New York University, New York, N.Y.

[21] Appl. No.: 481,956

[22] Filed: Jun. 7, 1995

[51] Int. Cl.$^6$ .............................. A01H 5/00; C12N 15/29; C12N 15/82; C12N 5/04

[52] U.S. Cl. ....................... 800/205; 536/23.6; 536/24.1; 435/69.1; 435/70.1; 435/172.3; 435/320.1; 435/419

[58] Field of Search .................................. 536/23.6, 24.1; 435/69.1, 70.1, 172.3, 240.4, 320.1, 419; 800/205

[56] References Cited

PUBLICATIONS

Minakami et al., 1994, "Molecular Cloning and the Functional Expression of Two Isoforms of Human Metabotropic Glutamate Receptor Subtype 5", Biochem Biophys Res Commun 199:1136–1143.
Newman et al., 1994, "Genes Galore:A Summary of Methods for Accessing Results from Large–Scale Partial Sequencing of Anonymous Arabidopsis cDNA Clones", Plant Physiol 106:1241–1255.
Lam et al., 1994, "Metabolic Regulation of the Gene Encoding Glutamine–Dependent Asparagine Synthetase in *Arabidopsis thaliana*", Plant Physiol 106:1347–1357.
Nakanishi et al., 1994, "Molecular Diversity of Glutamate Receptors and their Physiological Functions", *Toward a Molecular Basis of Alcohol Use and Abuse*, ed. by Jansson et al., pp. 71–80.
Condorelli et al., 1994, "Glutamate Receptor–Driven Activation of Transcription Factor in Primary Neuronal Cultures", Neurochem Res 19:489–499.
Kuryatov et al., 1994, "Mutational Analysis of the Glycine–Binding Site of the NMDA Receptor: Structural Similarity with Bacterial Amino Acid–Binding Proteins", Neuron 12:y1291–1300.
Papp and Moryl, 1994, "Antidepressant Activity of Non–Competitive and Competitive NMDA Receptor Antagonists in a Chronic Mild Stress Model of Depression", Eur J Pharmacology 263:1–7.
Stern–Bach et al., 1994, "Agonist Selectivity of Glutamate Receptor Is Specified by Two Domains Structurally Related to Bacterial Amino Acid–Binding Proteins", Neuron 13:1345–1357.
Vincentz et al., 1993, "Regulation of Nitrate and Nitrite Reductase Expression in *Nicotiana plumbaginifolia* Leaves by Nitrogen and Carbon Metabolites", Plant J 3:315–324.
Seeburg, 1993, "The Molecular Biology of Mammalian Glutamate Receptor Channels", Trends in Neuro Sci 16:359–365.
Condorelli et al., 1993, "Induction of Primary Response Genes by Excitatory Amino Acid Receptor Agonists in Primary Astroglial Cultures", J Neurochem 60: 877–885.

Kohler et al., 1993, "Determinants of $Ca^{2+}$ Permeability in Both TM1 and TM2 of High Affinity Kainate Receptor Channels: Divesity by RNA Editing", Neuron 10:491–500.
Cunningham et al., 1993, "Excitatory Amino Acid Receptors: A Gallery of New Targets For Pharmacological Intervention", Life Sci 54:135–148.
Schoepp and Conn, 1993, "Metabotropic Glutamate Receptors in Brain Function and Pathology", Trends in Pharmacol Sci 14:13–20.
Kanai et al., 1993, "The Elusive Transporters With a High Affinity for Glutamate", Trends in Neuro Sci 16:365–370.
O'Hara et al., 1993, "The Ligand–Binding Domain in Metabotropic Glutamate Receptors is Related to Bacterial Periplasmic Binding Proteins", Neuron 11:41–52.
Burnashev et al., 1992, "Divalent Ion Permeability of AMPA Receptor Channels Is Dominated by the Edited Form of a Single Subunit", Neuron 8:189–198.
Gasic and Hollmann, 1992, "Molecular Neurobiology of Glutamate Receptors", Annu Rev Physiol 54:507–536.
Baskys, 1992, "Metabotropic Receptors and 'Slow' Excitatory Actions of Glutamate Agonists in the Hippocampus", Trends in Neuro Sci 15:92–96.
Sommer et al., 1991, "Flip and Flop: A Cell–Specific Functional Switch in Glutamate–Operated Channels of the CNS", Science 249:1580–1585.
Hume et al., 1991, "Identification of a Site in Glutamate Receptor Subunits That Controls Calcium Permeability", Science 253:1028–1031.
Sommer et al., 1991, "RNA Editing in Brain Controls a Determinant of Ion flow in Glutamate–Gated Channels", Cell 67:11–19.
Lea et al., 1990, in: *The Biochemistry of Plants*, vol. 16, ed. by Stumpf and Conn: Plenum Press, pp. 121–155.
Graham et al., 1990, "Injection of Excitatory Amino Acid Antagonists Into the Medial Pallidal Segment of a 1–Methyl–4Phenyl–1,2,3,6–Teterahydropyridine (MPTP) Treated Primate Reverses Motor Symptoms of Parkinsonism", Life Sci 47:PL–91–PL–97.
Kennedy, 1989, "Regulation of the Synaptic Transmission in the Central Nervous System: Long Term Potentiation", Cell 59: 777–787.
Monaghan et al., 1989, "The Excitatory Amino Acid Receptors: Their Classes, Pharmacology, and Distinct Properties in the Function of the Central Nervous System", Annu Rev Pharmacol Toxicol 29:365–402.
Choi, 1988, "Glutamate Neurotoxicity and Diseases of the Nervous System", Neuron 1:623–624.

(List continued on next page.)

*Primary Examiner*—David T. Fox
*Attorney, Agent, or Firm*—Pennie & Edmonds LLP

[57] ABSTRACT

The present invention relates to a family of GluR in plants, including ionotropic (iGluR), metabotropic (mGluR) and other glutamate-like plant receptors. The plant GluRs of the invention may function as signal transducers involved in the regulation of plant growth. The invention also relates to the identification of compounds that modulate the activity of the plant GluR, and the use of such compounds as plant growth regulators, including herbicides.

8 Claims, 19 Drawing Sheets

PUBLICATIONS

Saur et al., 1987, "The Effect of Phosphinothricin (Glufosinate) on Photosynthesis II.The Causes of Inhibition of Photosynthesis", Z Naturforsch 42:270–278.

Balke, 1985, "Herbicide Effects on Membrane Function", *Weed Physiology,* CRC Press, Inc., pp. 113–139.

Urquhart and Joy, 1981, "Use of Phloem Exudate Technique in the Study of Amino Acid Transport in Pea Plants", Plant Physiol 68:750–754.

Ratajcak, et al., 1981, "The Effect of Different Carbon and Nitrogen Sources on the Activity of Glutamine Synthetase and Glutamate Dehydrogenase in Lupine Embryonic Axes", Physiol Plant 51:277–280.

Lea and Miflin, 1980, *The Biochemistry of Plants,* vol. 5, ed. by Stumpf and Conn, Academic Press, pp. 569–607.

Seeburg, 1995, "The Molecular Biology of Mammalian Glutamate Receptor Channels", TINS 16:359–365.

Lam et al., 1994, Metabolic Regulation of the Gene Encoding Glutamine–Dependent Asparagine Synthetase in *Arabidopsis thaliana,* Plant Physiol. 106:1347–1357.

Nakanishi et al., 1994,"Molecular Diversity of Glutamate Receptors and their Physiological Functions", *Toward a Molecular Basis of Alcohol Use and Abuse* (Birkhauser, Boston) pp. 71–80.

Stern–Bach et al., 1994, "Agonists Selectivity of Glutamate Receptor Is Specified by Two Domains Structurally Related to Bacterial Amino Acid–Binding Proteins", Neuron 13:1345–1357.

Condorelli et al., 1993, "Induction of Primary Response Genes by Excitatory Amino Acid Receptor Agonists in Primary Astroglial Cultures", J. Neurochem. 60:877–885.

Cunningham et al., 1993, "Excitatory Amino Acid Receptors: A Gallery of New Targets for Pharmacological Intervention", Life Sciences 54:135–148.

Schoepp et al., 1993, "Metabotropic Glutamate Receptors in Brain Function and Pathology", Trends in Pharmacol. Sci. 14:13–20.

Vincentz et al. "Regulation of Nitrate and Nitrite Reductase Expression in *Nicotiana plumbaginifolia* Leaves by Nitrogen and Carbon Metabolites", 1993, Plant J. 3:315–324.

Baskys, 1992, "Metabolic Receptors and Slow Excitatory Actions of Glutamate Agonists in the Hippocampus", TINS 15:92–96.

Burnashev et al., 1992, "Divalent Ion Permeability of AMPA Receptor Channels Is Dominated by the Edited Form of a Single Subunit", Neuron 8:189–198.

Gasic et al., 1992, "Molecular Neurobiology of Glutamate Receptors", Annu. Rev. Phuysiol. 54:507–536.

Sommer et al., 1991, "RNA Editing in Brain Controls a Determinant of Ion Flow in Glutamate–Gated Channels", Cell 67:11–19.

Sommer et al., 1990, "Flip and Flop: A Cell–Specific Switch in Glutamate–Operated Channels of the CNS", Science 249:1580–1585.

Tsai et al., 1990, "Dark–Induced and Organ–Specific Expression of Two Asparagine Synthetase Genes in *Pisum sativum*", EMBO 9:323–332.

Kennedy, 1989, "Regulation of Synaptic Transmission in the Central Nervous System: Long–Term Potentiation", Cell 59:777–787.

Lea et al., 1988, "The Use of Mutants Lacking Glutamine Synthetase and Glutamate Synthase to Study Their Role in Plant Nitrogen Metabolism", *Recent Advances in Phytochemistry* (Plenum Press, New York) pp. 157–189.

Ross et al., 1988, "Excitoxic Principles of Plants Linked to Neuronal Diseases Involving Motor and Other Systems", *Frontiers in Excitatory Amino Acid Research* (Alan R. Liss, Inc., New York) pp. 517–521.

Saur et al. 1987, "The Effect of Phosphinothricin (Glufosinate) on Photosynthesis II. The Causes of Inhibition of Photosynthesis", Z. Naturforsch. 42:270–278.

Ratajczak et al., 1981, "The Effect of Different Carbon and Nitrogen Sources on the Activity of Glutamine Synthetase and Glutamate Dehydrogenase in Lupine Embryonic Axes", Physiol. Plant 51:277–280.

Urquhart and Joy, 1981, "Use of Phloem Exudate Techniques in the Study of Amino Acid Transport in Pea Plants", Plant Physiol. 68:750–754.

Lea and Miflin, 1980, "Transport and Metabolism of Asparagine and Other Nitrogen Compounds within the Plant", *The Biochemistry of Plants* (Academic Press, New York) pp. 569–607.

Anis et al., 1979, "Plant Lectins and Desensitization of Locust Glutamate Receptors", J. Physiology 291:47P.

Mache et al. 1992. EMBL Accession #Z18206.

Desprez et al. Mar. 1994. EMBL Accession #Z 30902.

| | Metabolic Conditions | Nitrogen Flow | Active Genes |
|---|---|---|---|
| A | LIGHT or High Sucrose → High C:N | N → Gln + Glu | GLN2, GLU1 |
| B | DARK or Low Sucrose → Low C:N | N → Gln → Asn, Gln → Glu → $NH_4^+$ | ASN1, GDH |

FIG. 4

| | | | | | | | |
|---|---|---|---|---|---|---|---|
| BACTERIA | E. COLI GlnH (58-98) | | QTKNVDLALAGITITDERKKAIDFSDGYYKSGLLVMVKANN | | | | |
| ANIMAL | CHICK KBP (90-130)<br>FROG KBP (89-129)<br>RAT GluR-K1 (464-504)<br>RAT GluR-K2 (470-510)<br>RAT GluR-K3 (468-508) | | LRQEADIAVAPLTVTSAREEVVSFTTPFLQTGIGILLRKET<br>IRKEADLAIAPLTIITSVRENAISFTKPFMQTGIGILLKKDT<br>VYGRADVAVAPLTITLVREEVIDFSKPFMSLGISIMIKKPQ<br>VYGRADIAVAPLTITLVREEVIDFSKPFMSLGISIMIKKPQ<br>VYGKADIAIAPLTITLVREEVIDFSKPFMSLGISIMIKKPQ | | | | |
| | | | * * * * * * * * * * * * | | | | |
| PLANT | ARABIDOPSIS GluR | | QRDKYDAAVGDITITSNRSLYVDFTLPYTDIGIGILTVKKK | | | | |

FIG. 6

```
                        10        20        30↓      40
At-iGluR        RGNNDNLAYLLSTQRDKYDAAVGDITITSNRSLYVDFTLPYT
                |||::||:::||  |||::|:::
NMDA         YLVTNGKHGKKVNNVWNGMIGEVVYQRAVMAVGSLTINEERSEVVDFSVPFV
             530       540       550       560       570       580

┌───── TMI ──────────
                50        60       │70        80
At-iGluR     DIGIGILTVKKKSQ-GMWTFFDPFEKSLW-LASGAFFVLTGIVVWLVE--
             :||::::  ::::  :  :|::||:  ||:|         ||    |
NMDA         ETGISVMVSRSNGTVSPSAFLEPFSASVWVMMPVMDLIVSAIAVFVFEYF
             590       600       │610       620      │630

┌── TMII ──↓
               90        100      │110       120│
At-iGluR     RPV--NPEF---QGSWGQQLSMMLLVWILLPLQLLTGEKLQK---MSSRF
             :||   |:::    :::   |: ::     |||        :|:    :|:
NMDA         SPVGYNRNLAKGKAPHGPSFTIGKAIWLLWGLVFNNSVPVQNPKGTTSKI
             640       650      │660      │670       680

─── TMIII ──────────────────────
               140       150        160       170       180
At-iGluR     LVIVWVFVVLILTSSYSANLTSTKTISRMQLNHQMVFGGSTTSMTAKLGSINGG
             :| |||  |   |  |||::    :  ::   :|:    :|  ::::  ::  ::
NMDA         MVSVWAFFAVIFLASYTANLAA--FMIQEEFVDQV--TGLSDKKFQRPHDYSPP
             690       700       710       720       730

190       200       210       220
At-iGluR     GGLCTTLRDGTLTHVINEIPYLSILIGNYPNDFVMTDRVTNTNGF
              : |: :::|  ::  |:  ||:     :::: ::  | ::  |: ::|
NMDA         FRFGTVPNGSTERNIRNNYPYMHQYMTKFNQKGVEDALVSLKTGK
             740       760       770       780

TMIII
              230       240       250       260
At-iGluR     --GFMFQKGSDLVPKVSREIA-KLRSLGMLKDMEEK
              :|::: ::  |   |:::|: :  || ::|
NMDA         LDAFIYD-AAVLNYKAGRDEGCKLVTIGSGYIFATTGYGIALQKGSPWK
             790       800       810       820

10        20        30↓
At-iGluR        RGNNDNLAYLLSTQRDKYDAAVGDITITSNRSLYVDFT
                :|  ||:  :|||    |:    :||:
KA           SYEIRLVEDGKYGAQDDKGQWNGMVKELIDHKADLAVADLTITHVREKAIDFS
             450       460       470       480       490       500
```

FIG.7A(1)

```
              40         50         60       70 ┌──────── TM I ────────
At-iGluR  LPYTDIGIGILTVKKK--SQGMWTFFDPFESSL│WL--------ASGAFF
          |: ::|::||  | :  ::::::|::|:: ::│|:      :|:::
KA        KPFMTLGVSILYRKPNGTNPSVFSFLNPLSPDI│WMYVLLAYLGVSCVLF
             510        520        530     │  540        550
                                            └──────────────────

┌─────────────────────────────┐  ┌──── TM II ──↓
              80        │90        100  │    110       120│
At-iGluR  VLTGIVV--WLVE│RPVNPEFQGSWGQQLS│MMLLVWILLPLCLLTG│EKL--Q
           :    |   :: │ |  ||:  :  ::::│|:   |: :    ::│| :
KA        VIARFSPYEWYDA│HPCNPGSEVV-ENNFT│LLNSFWFGMCSLMQQC│SELMPK
             560       │  570       580 │  590           │600
          └────────────┘                └────────────────┘

┌──── TM III ────┐
              130        │140        150  │ 160        170
At-iGluR  KMSSR│FLVIVWVFVVLILTSSYSA│NLTSTKTISRMQLNHQMVFGGSTTSMT
          :|:||::   :|   ::||::|||:|||::  |::||:   : :  :: :
KA        ALSTR│IIGGIWWFFTLIIISSYTA│NLAAFLTVERMESPIDSA-DDLAKQTK
             610│       620        │630         640        650
             └──────────────────────┘

180        190        200        210        220
At-iGluR  AKLGSINGGGGLCTTLRDGTLTHVINEIPYLSILIGNYPNDFVMTDRVTNT
           :   |::::|:::  |  ::::::   :  :::|   :: ::   : ||
KA        IEYGAVKDGATH-TFFKKSKISTFEKMWAFMSSKPSALVKNNEEGIQRTLT
             660        670        680        690        700

230        240        250        260
At-iGluR  NGFGFMFQKGS-DLVPKVSREIAKLRSLGMLKDMEEK
          :::::::::::  : ::: : :::::::       :|
KA        ADYALLMESTTIEYITQRNCNLTQIGGLIDSKGYGIGTPMGSPYR
             710        720        730        740
```

FIG.7A(II)

```
                        *           *              **    *
              520       530       540       550        560       570
Mgr7_R    GKGVREIPSSVCTLPCKPGQRKTQKGTPCCWTCEP-CDGYQYQFDEMTCQHCPYDQRPN
                                      ||  ::  |:  :|::::       ||  |  ::
ARABIDOPSIS                       TFXCWLKNAFCASSFFQLSSME----PYRLRLR
                                         10        20

580       590       600       610       620       630
Mgr7_R    ENRTGCQNIPIIKLEWHSPWAVIPVFLAMLGIIATIFVMATFIRYNDTPIVRASGRELSY
           : |:  |: :  |   ::  |  | : |:: ||: ::  :  :| ::  :|
ARABIDOPSIS FSFQKC-SIAAF-LGPAVSFNSIERFLNSLS-TSLIFVXFSSMYF--LSXTCSSSIIFSV
             30        40         50         60        70        80

640       650       660       670       680       690
Mgr7_R    VLLTGIFLCYIITFLMIAKPDVAVCSFRRVFLGLGMCISYAALLTKTNRIYRIFEQGKKS
           :::  ||    ||
ARABIDOPSIS XVITGAFLARPSAPISAFSFGSDAIISFSLK
             90        100       110
```

FIG. 7B

EST # ATT50711

```
     TGAAGATGCA GGACAGGTTC AATGGAGGTA TGATAACCCT CCAGACTTCA
 51  ATAGTGTGAA CCAGCTCTTT GAAGAAGGCC AGACTAAGGT GTGGCCAGAA
101  GGTTCGTTAG AAGAGACAGT GCAAAACGCG ATCAAGTCAT GGGAGATGGA
151  GTTCTCACAT AAGATCCGTT TACAGGACTT CAAGACTATA AACCCTGAGA
201  AGTTTAAGCT CTTTTGTCAA TGGGAGAGAA GGTTT
```

EST# ATT52655

```
  1  GGTGAATCTT TCGAGGTTGA GGAGGCGGTG GCTCTCGAGT CACAAACCAT
 51  AGCGCATATG GTTGAAGACG ACTGCGTNAN CAACGGAGTC CCTCTTCCTA
101  ACGTCACGAG CAAGATCCTN GCCAAGGTGA TCGAGTATTG CAAGAGGCAC
151  GTCGAGGCTG CTGCCTNTAA AGGCCGA
```

EST# T20773

```
  1  TCGTTTGCTC GAAGATCCGC TGCTTGATCT GCTCGCCACA CGCTATNGGA
 51  GAGGNAANGG TTAGGGTTAC TNATTTTCCG TCGAGTAGTC TNACNNAAAA
101  CTGCAACGGC TTACAACTTT GATCCGCCAT CGATTTTCGA TTCTAAAGCT
151  TGGACGAAGN AGAAGNANAA AGTTCGATTC GATTTCTGGA GAGAAATTGG
201  GGGAAAGTTT AAAAACGGAT CCCTAAGGTA GTCTGAGTCT CTCTCTC
```

FIG. 7C

| LANES | TREATMENTS | AVERAGE FOLD INDUCTION OF ASN1 RELATIVE TO CONTROL (LANE 3) |
|---|---|---|
| 4 | +0.3 mM KAINATE | 1.82 +/- 0.05 |
| 5 | +0.03 mM KAINATE | 1.97 +/- 0.02 |
| 6 | +0.05% GLUTAMATE | 2.46 +/- 0.40 |

PLANT GLUTAMATE RECEPTORS

This invention was made with U.S. government support under NIH grant GM-32877. The U.S. government has certain rights in the invention.

1. INTRODUCTION

The invention relates to a family of glutamate receptors (GluR) in plants, compounds that modulate the activity of the plant GluR, and the use of such compounds as plant growth regulators, including herbicides. The invention also relates to nucleotide sequences encoding the plant GluR and to plant assay systems designed to identify novel plant growth regulators that may be used as herbicides and/or pharmaceutical drugs.

2. BACKGROUND OF THE INVENTION

2.1. METABOLIC AND REGULATORY ROLES OF GLUTAMATE IN PLANTS

Glutamate has important roles in plant nitrogen metabolism. Glutamate is the amino acid into which inorganic nitrogen is first assimilated into organic form. Plants have three distinct nitrogen processes related to nitrogen metabolism: (1) primary nitrogen-assimilation, (2) photorespiration, and (3) nitrogen "recycling." All three processes involve assimilation of ammonia into glutamate and glutamine by the operation of glutamine synthetase (GS) and glutamate synthase (GOGAT). Glutamate and glutamine, being the first products of nitrogen-assimilation, in turn serve as nitrogen donors in the biosynthesis of essentially all amino acids, nucleic acids, and other nitrogen-containing compounds such as chlorophyll (Lea et al., in: *Recent Advances in Phytochemistry*, edited by Poulton et al., New York and London: Plenum Press, 1988, pp. 157–189).

Glutamate is also a principal "nitrogen-transport" compound in plants. It and glutamine are two of only four amino acids used to transport nitrogen within a plant (Lea and Miflin, in: *The Biochemistry of Plants*, Vol. 5, edited by Stumpf and Conn, Academic Press, 1980, pp. 569–607; Urquhart and Joy, 1981, Plant Physiol. 68:750–754). In light-grown metabolically active plants, glutamate and glutamine are used in anabolic reactions and are transported as such. By contrast, in etiolated or dark-adapted plants, glutamine is converted into inert asparagine for long-term nitrogen storage.

Glutamate also may be a signal or regulatory molecule in regulating the expression of plant genes. Specifically, glutamate along with glutamine and asparagine appears to have an antagonistic role to that of sucrose in regulating certain nitrogen assimilation genes. Sucrose has been shown to induce the expression of genes for nitrate reductase (NR), nitrite reductase (NiR), and chloroplastic glutamine synthetase (GS2) in tobacco (Saur et al., 1987, Z. Naturforsch. 42:270–278; Vincentz et al., 1993, Plant J. 3:315–324). Sucrose also induces genes for GS2 and ferroredoxin-dependent glutamate synthase (Fd-GOGAT) in Arabidopsis. Sucrose-induction of the NR and NiR in tobacco is suppressed by subsequent additions of glutamine, glutamate or asparagine to the media (Vincentz et al., ibid.). Conversely, a nitrogen metabolism gene, glutamine-dependent asparagine synthetase (ASN1), in Arabidopsis is repressed by light or sucrose (Lam et al., 1994, Plant Physiol. 106:1347–1357). The sucrose repression of ASN1 can be relieved by additions of glutamine, glutamate, or asparagine (Id.). Sucrose induction of GS2 genes by asparagine and glutamine has been demonstrated in lupine embryos (Ratajcak, et al., 1981 Physiol. Plant 51:277–280).

2.2. GLUTAMATE RECEPTORS IN ANIMAL CELLS

Excitatory amino acids constitute the principal neurotransmitter receptors that mediate synaptic communication in animals (Gasic et al., 1992, Annu. Rev. Physiol. 54:507–536). In particular, L-glutamate is the major excitatory neurotransmitter of the mammalian central nervous system (Monaghan et al., 1989, Annu. Rev. Pharmacol. Toxic. 29:365–402). Glutamate signaling in animals is important for many physiological and pathological processes such as developmental plasticity, long-term potentiation, and excitotoxic damage in ischemia and other neurodegenerative disorders (Choi, 1988, Neuron 1:623–624; Kennedy, 1989, Cell 59:777–787).

In animals, glutamate can trigger various downstream physiological responses by interacting with different GluR. GluRs in animals are involved in central nervous system (CNS) disorders such as Huntington's disease, Parkinson's disease and Alzheimer's disease. The GluR is involved in the initiation and propagation of seizures and in massive neuronal cell death during periods of ischemia and hypoglycemia. GluRs have been grouped into five distinct subtypes (Gasic et al., 1992, Annu. Rev. Physiol. 54:507–536): (a) NMDA (N-methyl-D-aspartate), (b) KA (Kainate), (c) AMPA (alpha-amino-3-hydroxy-5-methyl-4-isoxazole propionate), (d) L-AP4 (2-amino-4-phosphonobutyrate) and (e) ACPD (trans-1-amino-cyclopentane-1,3 dicarboxylate). NMPA, KA and AMPA, which form ligand gated ion channels that are activated on a msec scale, are the ionotropic (iGluR) subtypes. By contrast, metabotropic (mGluR) subtypes, L-AP4 and ACPD, are coupled to G proteins and operate on a time scale of several hundred msec to seconds. LAP-4 receptor probably acts via a G protein by increasing the hydrolysis of cGMP and subsequently leads to the closure of ion channels conducting an inward current. The ACPD subtype, which couples with a G protein that is linked to inositol phosphate/diacylglycerol formation and subsequent release of calcium from internal stores. Both iGluR and mGluR seem to play a role in the activation of transcription factors, such as c-jun and c-fos (Condorelli et al., 1993, J. Neurochem. 60:877–885; Condorelli et al., 1994, Neurochem. Res. 19:489–499).

2.2.1. IONOTROPIC GLUTAMATE RECEPTORS

There are major differences in the neurophysiological functions of the three subtypes of iGluR (Seeburg, 1995, TINS 16:359–365). AMPA receptors are found in the majority of all fast excitatory neurotransmission. The very low Ca++ permeability of AMPA receptor suggests that they probably do not trigger biochemical reactions via an increase in intracellular Ca++ levels. In NMDA receptor, Ca++ flux will trigger different processes ranging from trophic developmental actions to an activity-dependent resetting of the synaptic strength underlying some forms of learning and memory. The significance of high-affinity kainate sites in the nervous systems is yet to be fully understood.

(A) AMPA receptor

AMPA receptors consist of at least four different subunits: GluR1–GluR4. The two major forms, named "flip" and "flop", which are formed by differential splicing, display different expression profiles in the mature and the developing brain (Sommer et al., 1990, Science 249:1580–1585). For GluR2 subunit, RNA editing (Q to R) in transmembrane domain (TM) II has been shown to regulate the Ca++ permeability. RNA editing leads to a decrease in Ca++ permeability (Burnashev et al., 1992, Neuron, 8:189–198; Hume et al., 1991, Science 253:1028–1031).

(B) Kainate Receptors

High-affinity kainate receptors are composed of subunits GluR5–GluR7, KA1, and KA2 (Seeburg et al., 1995, TINS 16:359–365). Both GluR5 and GluR6 subunits also display the Q to R editing similar to the case of GluR2 of AMPA receptors (Sommer et al., 1991, Cell 67:11–19). GluR6 has two additional positions in TMI that are modified by RNA editing (Kohler et al., 1993, Neuron 10:491–500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6(Q) channels (Kohler et al., 1993, Neuron 10:491–500).

(C) NMDA receptor

NMDA receptors are highly permeable to Ca++. The NMDA receptor can be reconstituted as heteromeric structures from two subunit types: NRI and one of the four NR2 (NR2A–NR2D) (Seeburg, 1995, TINS 16:359–365). All of the subunits do not show RNA editing in TMI and TMII. In fact all subunits contain an N at the site which Q to R editing occurs in non-NMDA iGluR. The most distinct feature of NMDA receptors is that they require both glycine and glutamate or both glycine and NMDA to activate the channel. The NMDA receptor has been linked to regulation of coccidian rhythm in rat brains.

2.2.2. METABOTROPIC GLUTAMATE RECEPTORS

In contrast to ionotropic glutamate receptors (iGluR) the hallmark of the mGluR receptors resides on the fact that these molecules are coupled to G proteins and thus able to elicit typical G protein-driven intracellular responses (Gasic et al., 1992, Annu. Rev. Physiol. 54:507–536; Minakami et al., 1994, Biochem. Biophys. Res. Commun. 199:1136–1143; Schoepp et al., 1993, Trends in Pharmacol. Sci. 14:13–20).

The cloning of mGluR1 from a expression cDNA library of a rat cerebellum (mGluR1α), was followed by the cloning and characterization of six other mGluR genes (Schoepp et al., 1993, Trends in Pharmacol. Sci. 14:13–20). The mGluR1a, the prototype member of the family, possess a large extracellular domain, a putative "seven pass" transmembrane region and display highly conserved amino acids with other members of the mGluRs both at the membrane spanning region, extracellular region and intracytoplasmic loops between transmembrane domains (Gasic et al., 1992, Annu. Rev. Physiol. 54:507–536; Minakami et al., 1994, Biochem. Biophys. Res. Commun. 199:1136–1143; Schoepp et al., 1993, Trends in Pharmacol. Sci. 14:13–20). The mGluR genes are unique in that they do not show significant homology with any of the previously characterized G proteins (Nakanishi et al., 1994, In: Toward a molecular basis of alcohol use and abuse. ed. by Jansson et al. p 71–80; Schoepp et al., 1993, Trends in Pharmacol. Sci. 14:13–20) and very little is known on the signal transduction mechanisms and second messenger responses for each mGluR receptor (Schoepp et al., 1993, Trends in Pharmac. Sci. 14:13–20).

Studies in the in situ localization of mRNA encoding the different mGluRs shows them to be differentially distributed in the brain with cells from diverse tissues expressing one or more combinations of the various members of the mGluR family of receptors, suggestive of a relevant participation in the modulation of several important biological processes (Schoepp et al., 1993, Trends in Pharmac. Sci. 14:13–20). Indeed, the mGluR proteins have been reported to be involved with neuroprotection and neuronal pathophysiology (Baskys, 1992, Trends in Neuro Sci. 15:92–96; Schoepp et al., 1993, Trends in Pharmac. Sci. 14:13–20).

Analysis of the pharmacological properties of the individual mGluR molecules revealed that the agonists L-AP4 (L-2-amino-4-phosphonobutyrate) and ACPD (trans-1-amino-cyclopentane-1,3 dicarboxylate) can selectively stimulate different mGluR serving as a basis for the classification of this group of proteins (Nakanishi et al., 1994, In: Toward a molecular basis of alcohol use and abuse. Ed. Jansson et al. p 71–80).

(A) L-AP4 receptor

The L-AP4 receptor has been defined electrophisologically as an inhibitory glutamate site and biochemical evidence suggest that mGluR4, mGluR6 and mGluR7 are involved in this response (Nakanishi et al., 1994, In: Toward a molecular basis of alcohol use and abuse ed by Jansson et al. p 71–80; Schoepp et al., 1993, Trends in Pharmacol. Sci. 14:13–20). The L-AP4 receptor appears to be localized pre-synaptically such that activation inhibits the release of excitatory neurotransmitter through a mechanism involving a pertussis toxin sensitive G protein (Nakanishi et al., 1994, In: Toward a molecular basis of alcohol use and abuse. Ed. Jansson et al. p 71–80). The molecular identity and possible biological function of this group of receptors come from studies where mammalian cells were transfected with a cloned isoform of mGluR (mGluR4) responded to both L-glutamate and L-AP4 by depressing forskolin-stimulated cAMP levels (Nakanishi et al., 1994, In: Toward a molecular basis of alcohol use and abuse. ed. by Jansson, p 71–80; Schoepp et al., 1993, Trends in Pharmacol. Sci. 14:13–20). L-AP-4 has also been shown to reduce electrically-stimulated excitatory transmission, suggestive of a close interaction between mGluR and $Ca^{2+}$ channels (Cunningham et al., 1993, Life Sciences 54:135–148; Schoepp et al., 1993, Trends in Pharmac. Sci. 14:13–20) and specifically in the regulation of ionotropic glutamate receptors (Baskys, 1992, Trends in Neuro. Sci. 15:92–96). Very little is known about the signal transduction mechanisms and second messenger responses elicited by this subgroup of mGluR.

(B) ACPD receptor

The mechanisms of signal transduction of this subgroup of receptors is better understood than that of the L-AP4-responsive mGluRs. Transfection of the cDNA for mGluR1, mGluR2, mGluR3 and mGluR5 in CHO cells revealed that this receptors are strongly responsive to the drug ACPD (trans-1-amino-cyclopentane-1,3 dicarboxylate) (Cunningham et al., 1993, Life Sciences 54:135–148; Schoepp et al., 1993, Trends in Pharmac. Sci. 14:13–20). However, not all mGluR activate the same pathways and different mGluR can elicit diverse intracellular responses. Thus, mGluR5 possess high homology with mGluR1 yet these two receptors differ in which mGluR5 does not induce formation of cAMP. Moreover, stimulation of the mGluR2 and 3 does not lead to phosphoinositide hydrolysis and mGluR2 has been shown to inhibit cAMP formation in transfection experiments (Schoepp et al. 1993). The diversity of the mGluR family of receptors can be further appreciated by the recent observation that mGluR2 and mGluR3 receptors display an unusually high response to stimulation by quisqualate when compared to other ACPD mGluR responses (Nakanishi et al., 1994, In: Toward a molecular basis of alcohol use and abuse. ed. by Jansson et al. p 71–80; Schoepp et al., 1993, Trends in Pharmacol. Sci. 14:13–20) which argues in favor of their further grouping in a more specialized division among the ACPD-induced receptors. Finally, stimulation of primary neuronal cultures with ACPD and quisqualate caused a strong and transient induction of immediate early genes such as c-fos, c-jun and zif-268 mRNAs (Condorelli et al., 1994, Neurochem Res. 19:489–499).

3. SUMMARY OF THE INVENTION

The present invention relates to a family of GluR in plants, including ionotropic (iGluR), metabotropic (mGluR) and other glutamate-like plant receptors. The plant GluRs of the invention may function as signal transducers involved in the regulation of plant growth. The invention also relates to the identification of compounds that modulate the activity of the plant GluR, and the use of such compounds as plant growth regulators, including herbicides.

The invention is based in part, on a number of unanticipated surprising discoveries. One is the discovery of plant proteins that have high degree of amino acid sequence homology to the animal ionotropic or metabotropic glutamate receptors previously found only in vertebrate tissues. The other is the finding that agonists and antagonists of animal glutamate receptors function to modulate expression of plant genes and as plant growth regulators. These agonists and antagonists structurally do not resemble glutamate. Thus, their actions in plants likely are due to their specific interaction with one or more plant glutamate receptors, rather than to general effects on glutamate-utilizing enzymes. These findings together indicate that plants have glutamate receptors that function as signal transducers.

The invention encompasses: (a) nucleotide sequences that encode the plant GluR, including mutants, recombinants, and fusion proteins; (b) the expression of such nucleotide sequences in genetically engineered host cells and/or in transgenic plants; (c) the isolated GluR plant proteins and GluR engineered gene products, including mutants, fragments, and fusion proteins; (d) antibodies to the plant GluR proteins and polypeptides; (e) screening assays involving the use of plants, transgenic plants, genetically engineered cells that express the plant GluR or mutants thereof, or GluR proteins or peptides, to identify compounds that act as agonists or antagonists; (f) the use of such agonists or antagonists as plant growth regulators, including herbicides; (g) the engineering of transgenic plants resistant to herbicidal antagonists of the plant GluR and/or transgenic plants with improved agronomic or industrial properties; and (h) the use of antagonists or agonists of the plant GluR identified in the screening assays described herein as drugs for animal use, including humans.

3.1. DEFINITIONS

An agonist is defined herein as an agent that acts like a referenced compound or that activates a receptor molecule.

An antagonist is defined herein as an agent that acts in opposition to an agonist or a referenced compound or that inhibits a receptor molecule.

A chimeric gene comprises a coding sequence linked to a regulatory region, i.e., promoters, enhancer elements and additional elements known to those skilled in the art that drive and regulate expression, that said coding sequence is not naturally linked to. The coding sequence may encode messenger RNA (mRNA), antisense RNA or ribozymes.

4. BRIEF DESCRIPTION OF THE DRAWINGS

FIGS. 1A,1B,1C. HPLC Analysis of Free Amino Acids in Arabidopsis.

FIG. 1A. Amino acids were extracted from leaves of Arabidopsis plants that were grown in light (empty boxes) or subsequently dark adapted for 24 hours (filled boxes). Amino acids were derivatized and separated by reverse phase HPLC. Each sample represents the average of three different plants (two leaves/plant). The standard three letter code is used for all amino acids; gaba: γ-amino burytic acid.

FIG. 1B. Average amino acid content in phloem exudates of three independent plants (one leaf/plant).

FIG. 1C. Average amino acid content of xylem sap collected from cut hypocotyls of three independent plants. Data are from Schultz (1994).

FIG. 2. Reciprocal Control By Light On Arabidopsis GLN2 and ASN1 Expression

The effects of light on GLN2 and ASN1 expression were tested in mature Arabidopsis plants. Plants were grown on soil under a 16-h light/8-h dark cycle for 2 weeks and transferred to continuous light (lane 1) or continuous darkness (lane 2) for 5d. Total RNA (10 μg) was used for each of the lanes. Hybridization was performed by [α-$^{32}$P] dATP-labeled GLN2 or digoxigenin-labeled ASN1 DNA probes in Strategene QuikHyb solution under high stringency condition. The nylon filter was first hybridized with the GLN2 probe, then stripped, and rehybridized with the ASN1 probe. (Lam et al., 1994).

FIG. 3. Effect Of C:N Ratio On The mRNA Levels Of ASN1 And GDH

Arabidopsis seeds were grown on plates containing MS medium plus 3% (w/v) Suc under 16-h light/8-h dark cycle for 2 weeks. The plants were then transferred to media described below and grown in complete darkness for 2.5d. Lanes 1 to 4, MS medium with no sugar; lanes 5 to 8, MS medium with 3% (w/v) Suc. MS was supplemented with 0.4 mM Asn (lanes 2 and 6), 3.4 mM Gln (lanes 3 and 7), or 3.3 mM Glu (lanes 4 and 8). The expression of ASN1, GDH, and a cytosolic GS (GSR2) were detected by northern analyses (under high-stringency conditions in 50% [v/v] formamide solution). 10 μg of total RNA was used for each lane. The nylon filter was first hybridized with ASN1, then stripped, and re-hybridized with the GSR2 probe. The nylon filter was then stripped again and re-hybridized with the GDH probe.

FIG. 4. A Model Depicting The Regulation Of Nitrogen Assimilation Genes By C:N Ratio In the light, when photosynthesis occurs and carbon skeletons are abundant, nitrogen is assimilated and transported as glutamine and glutamate; levels of mRNA for genes involved in glutamine and glutamate synthesis (GLN2, GLU1) are accordingly induced by both light and sucrose. By contrast, light represses the synthesis of asparagine which therefore accumulates only in tissues of dark-adapted plants. Levels of ASN1 mRNA are dramatically induced in dark-adapted plants, and this induction is repressed by light or by high levels of sucrose. Thus, under conditions of carbon limitation or nitrogen excess, plants activate genes for asparagine biosynthesis (Lam et al., 1995). The mRNA level of GDH was found to be under similar control (see also FIG. 3).

FIG. 5. Proposed Topology and Functional Domains of Ionotropic Glutamate Receptor Subunits.

Hydrophobicity plots of GluR subunit sequences predict four transmembrane (TM) segments (TM I–IV), depicted here hypothetically as α helices I–IV.

FIG. 6. Peptide Sequence Homology Between The Arabidopsis iGluR (SEQ ID NO:1) and Animal iGluRs [E. coli GlnH: (SEQ ID NO:2); Chick KBP: (SEQ ID NO:3); Frog KBP: (SEQ ID NO:4); Rat GluR-K1: (SEQ ID NO:5); Rat GluR-K3:(SEQ ID NO:6); Rat GluR-K2:(SEQ ID NO:7)]. Peptide sequence analysis shows that the putative Arabidopsis iGluR contains a conserved glutamine binding domain which exists in all animal iGluRs.

FIG. 7A. Peptide sequence analysis shows the extensive homology between the putative Arabidopsis iGluR (SEQ ID NO:8) and animal iGluRs [NMDA: (SEQ ID NO:9); KA: (SEQ ID NO:10)]. The region of homology extends from the glutamine binding domain into the transmembrane domains.

FIG. 7B. Peptide sequence analysis shows the extensive homology between the putative Arabidopsis mGluR (SEQ ID NO:12) and animal iGluR (SEQ ID NO:11). The region of homology extends from the glutamate binding domain into the transmembrane domain.

FIG. 7C. Arabidopsis EST clones with low degree homology to glutamate binding domains. These EST clones have no homology to ionotropic nor metabotrobic GluR. Partial nucleotide sequence of EST clones are provided here [ATT50711:(SEQ ID NO:13); ATT52655:(SEQ ID NO:14); T20773:(SEQ ID NO:15)].

FIG. 8. Genomic Southern Analysis of Arabidopsis iGluR

Two μg of CsCl-purified Arabidopsis genomic DNA was digested with different restriction enzymes. Genomic Southern blot analyses were performed by running the digested DNA on a 1% (w/v) Tris-phosphate-EDTA agarose gel. The DNA was transferred to a nylon membrane after depurination, denaturation, and neutralization steps, followed by high-stringency hybridization with DIG-labeled probes which are generated by random-primed reactions (as described in the Boehringer-Mannheim Genius System User's Guide).

FIG. 9. Expression Of Arabidopsis iGluR In Different Tissues

Twenty μg of total RNA from each of the leaf, root, and flower tissues were run on a 1% formaldehyde agarose gel. Northern blot analyses were performed with high-stringency hybridization conditions at a temperature of 42° C. in 50% (v/v) formamide hybridization solution. Washing and chemiluminescent detection were performed according to the Boehringer-Mannheim Genius System User's Guide. The Northern shows that Arabidopsis iGluR mRNA is expressed predominantly in leaves and also at lower levels in roots and flowers of Arabidopsis.

FIG. 10. Chemical Structures of Glutamate, Kainate, and DNQX

FIG. 11A–11B. Effects Of iGluR Agonist and Antagonist On The Growth Of Arabidopsis Arabidopsis seeds were grown on MS+3% sucrose vertical tissue culture plates containing various amounts of kainate (A) or DNQX (B), with (white bars) or without (black bars) glutamate supplementation. The effects of each drug on plant growth were assayed by measuring root length after two week. The results were discussed in text.

FIG. 12A, 12B, 12C. Induction of Gene Expression by iGluR Agonist

FIG. 12A. Arabidopsis seeds were grown on plates containing MS medium plates 3% (w/v) Suc under 16-h light/ 8-h dark cycle for 2–3 weeks. The plants were then transferred to media described below and grown in complete darkness for 2d. All samples containing 3% sucrose except for lane 2. MS was supplemented with kainate (lane 4:0.3 mM and lane 5:0.03 mM), 0.05% (w/v) glutamate (lanes 6 and 7), and 10 μM DNQX (lanes 7 and 8). The expression of ASN1 and a control gene were detected by northern analyses on duplicate blots (under high-stringency conditions in 50% [v/v] formamide-solution), 20 μg of total RNA was used for each lane.

FIG. 12B. Quantitation of the Northern blot results in (A) by densitometry scan.

FIG. 12C. Average folds of induction in two Northern blot experiments.

FIG. 13A–13B. Inhibition of Arabidopsis Growth by High Dosage of Kainate and DNQX Photographic representation of high dosage inhibitory effects of kainate and DNQX on the growth of Arabidopsis as described in FIG. 11.

FIG. 14A–14B. Model Depicting Effects of Agonists and Antagonists on Plants Expressing Wildtype and Mutant GluR.

DETAILED DESCRIPTION OF THE INVENTION

Figure 1:
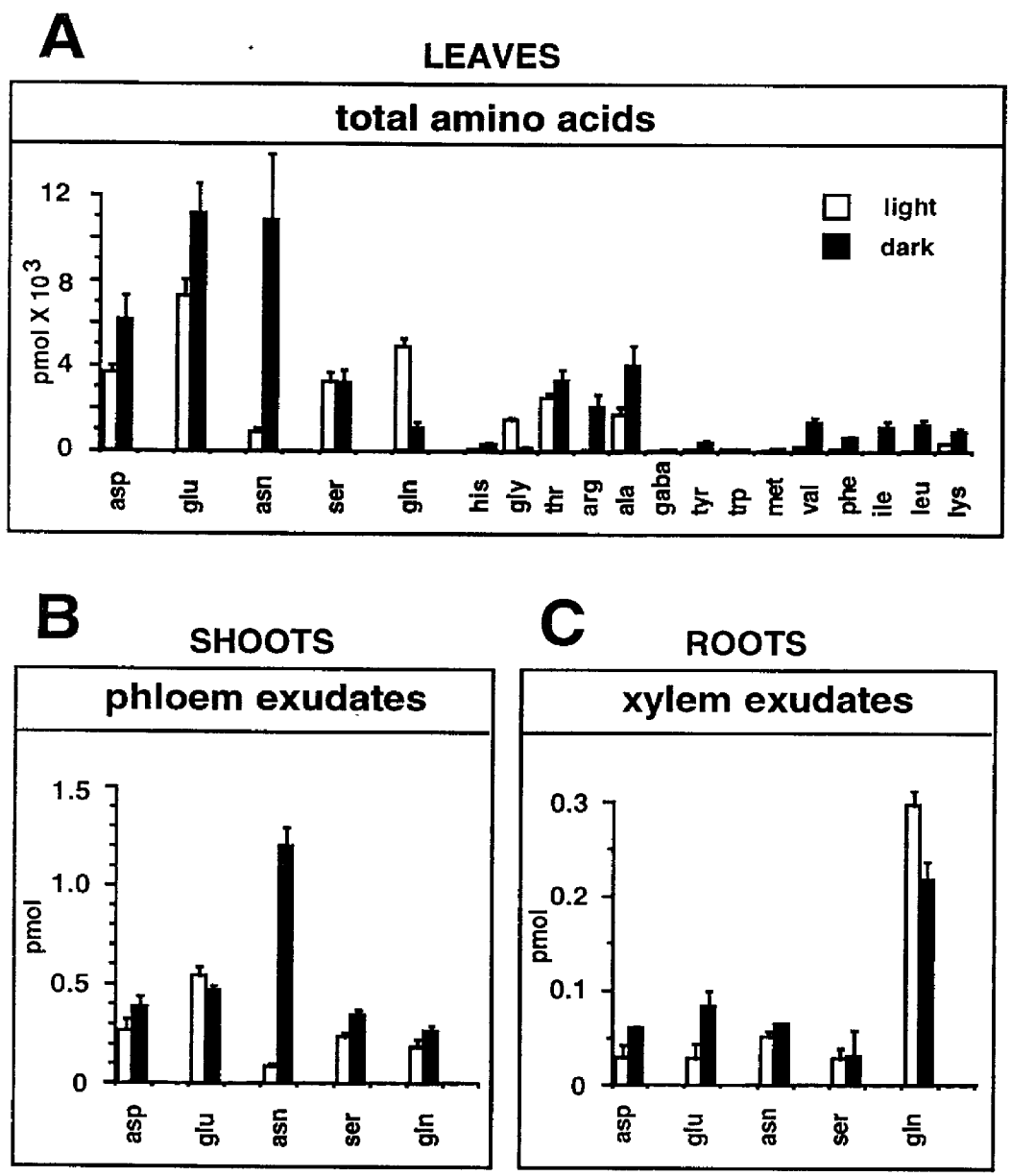
Figure 2:
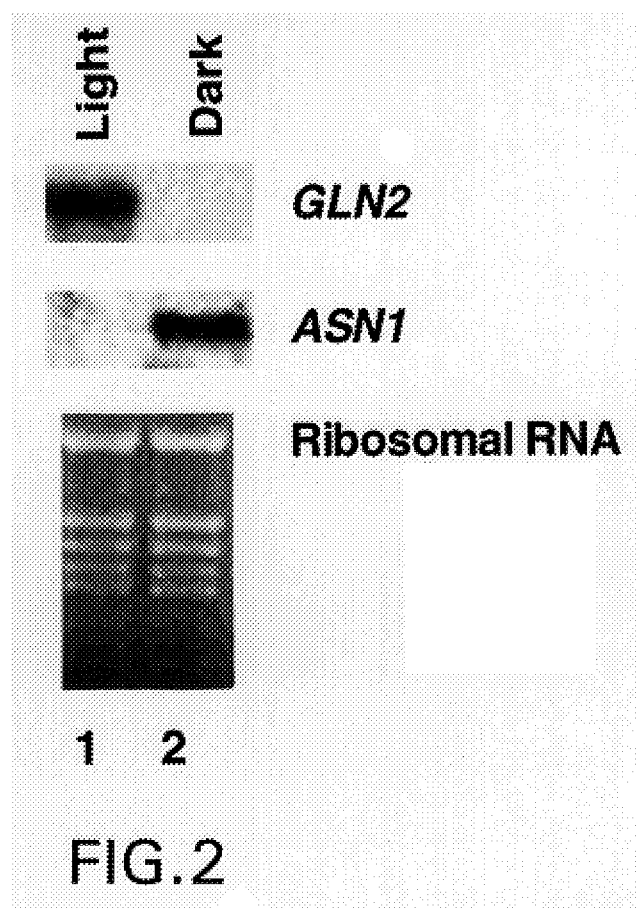
Figure 3:
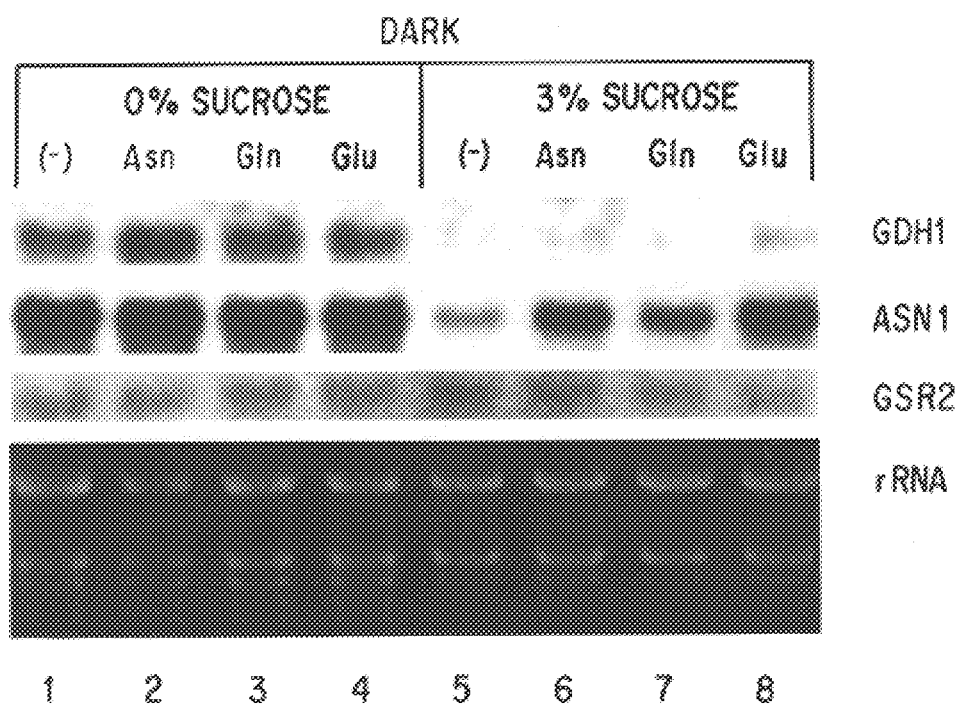

The present invention relates to a family of plant glutamate receptors, and glutamate-like receptors, the identification of compounds that modulate the activity of the plant GluR, and their use as plant growth regulators, including herbicides, or the identification of pharmaceutical agents used in animals, including man. The present invention is based, in part, on the discovery that glutamate may serve not only to transport nitrogen within a plant, but also act as a signaling molecule. A number of observations and discoveries described herein support the conclusion that the amide amino acids function as signaling molecules in plants. First, out of the 20 amino acids, only the amide amino acids, glutamate, glutamine, aspartate, and asparagine, accumulate to any significant levels as free amino acids in plant tissues, accounting for 64% of the total free amino acids in Arabidopsis leaves (FIG. 1). Second, out of the 20 amino acids only these four amide amino acids are found circulating within the plant vasculature to significant levels. Glutamate is the predominant amino acid transported within the phloem of light grown plants (FIG. 1 open bars). That glutamate may serve as a signaling molecule in plants is further supported by the fact that levels of free asparagine, glutamate, glutamine and aspartate are not static, but modulated by light. Glutamate levels are very high in the dark and low in the light (FIG. 1). In addition, the present invention is based on the discovery that glutamate, glutamine or asparagine each affects the expression of several nitrogen assimilatory genes in Arabidopsis (Lam et al., 1994, Plant Physiol. 106:1347–1357). These amino acids have also been shown to affect the expression of genes involved in nitrate reduction to ammonia (Vincentz et al., 1993, The Plant Journal 3:315–324).

The proposed role for glutamate is supported by the identification of two Arabidopsis cDNAs with striking identity to iGluR and mGluR found previously only in the animal nervous system. The Applicants identified two cDNA clones each with identity to a distinct type of animal glutamate receptor. One Arabidopsis cDNA clone (EST#107M14T7, pAt-iGR-1) shares high identity to a class of glutamate receptors called ionotropic (iGluR) receptors which constitutes ligand-gated ion channels (Gasic, G. P. and Hollmann, 1992, Annu. Rev. Physiol. 54:507–536; Kanai et al., 1993, TINS 16:365–370; O'Hara et al., 1993, Neuron 11:41–52; Seeburg, 1993, TINS 16:359–365). In animals, binding of glutamate to membrane bound iGluR stimulates the influx of Ca++ resulting in and fast excitatory neurotransmission which will subsequently cause a wide variety of downstream responses (Gasic and Hollmann, 1992, Annu. Rev. Physiol. 54:507–536; Kanai et al., 1993, TINS 16:365–370; O'Hara et al., 1993, Neuron 11:41–52; Seeburg, 1993, TINS 16:359–365). For example, iGluRs may play a role in the activation of transcription factors such as c-fos and c-jun in primary neuronal cultures (Condorelli et al., 1993, J. Neurochem. 60:877–885; Condorelli et al., 1994, Neurochem. Res. 19:489–499).

The invention also relates to a second Arabidopsis cDNA (EST#97C23T7, pAT-mGR-1) which shares identity to another class of animal glutamate receptors called metabotropic glutamate receptor, mGluR (Gasic and Hollmann, 1992, Annu. Rev. Physiol. 54:507–536). In animals, the mGluR class of glutamate receptors is coupled to a G protein that is linked to inositol phosphate/diacylglycerol formation which results in subsequent release of calcium from internal stores (Gasic, and Hollmann, 1992, Annu. Rev. Physiol. 54:507–536). In animals, mGluRs also have been reported to activate immediate early response genes, such as c-fos, c-jun, zif-268 (Condorelli et al., ibid).

Furthermore, the invention also relates to three additional Arabidopsis cDNAs (EST #T20773, ATT50711, AT52655), which share a low degree of homology to glutamate binding domains. These clones do not share identity with animal ionotropic and metabotropic GluRs. Therefore, they may represent a novel class of plant glutamate-like receptors.

Figure 10:
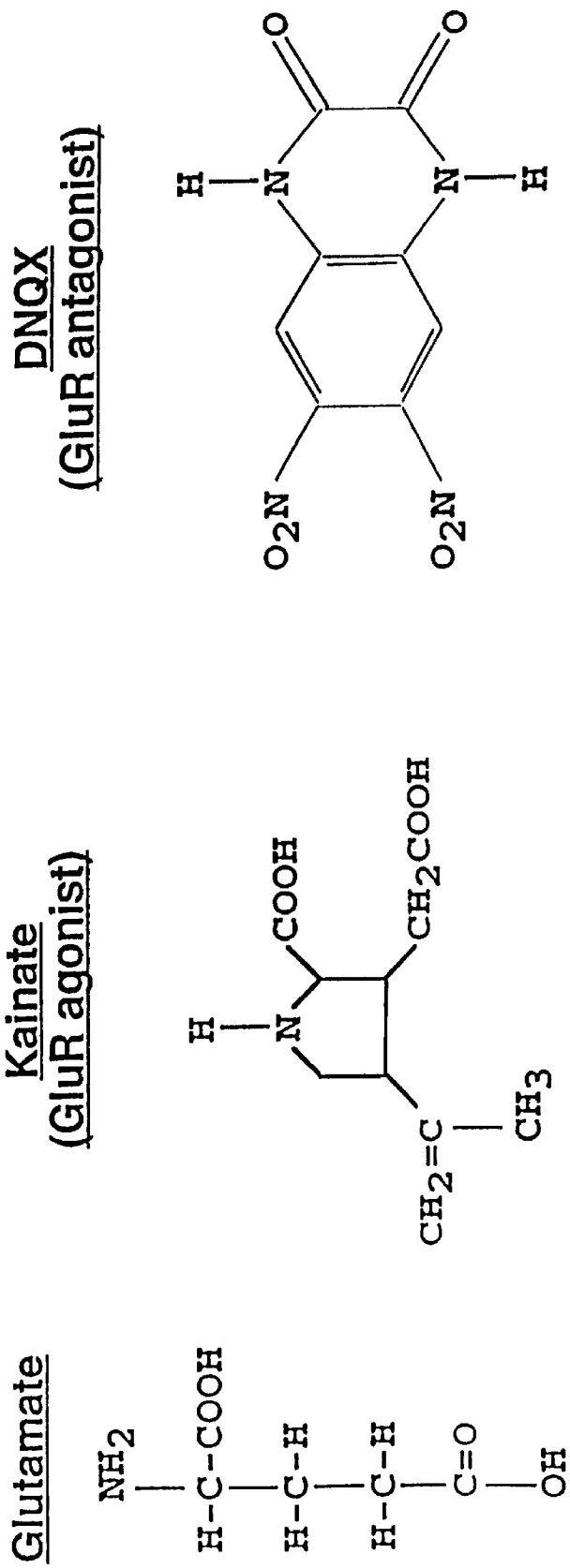

The present invention is also based on the Applicants' discovery that in addition to possessing GluR genes, plants possess functional GluRs. The Arabidopsis iGluR cDNA (pAt-iGR-1) shows high identity to the animal GluR specifically activated by an iGluR agonist called kainic acid (KA). The plant iGluR is unique in that it has homology to both NMDA-type and KA-type GluR in animals. These kainate-selective iGluR receptors are competitively inhibited by an iGluR antagonist called 6,7-dinitroquinoxaline (DNQX). This iGluR agonist (KA) and antagonist (DNQX) are structurally distinct from glutamate (see FIG. 10), yet they bind to the iGluR receptor and stimulate or inhibit its action. Thus, any responses which these drugs may effect in plants, are likely to be due to their specific interaction with a iGluR-type receptor, rather than to general effects caused by inhibition of glutamate-utilizing enzymes. This iGluR agonist/antagonist pair can specifically affect the expression of nitrogen metabolic genes in Arabidopsis. This data supports the notion that plants possess a functional GluR.

The invention also relates to the use of the plant GluR as a target to select for new herbicides. The cloned plant GluR described herein can be utilized for the selection of new plant specific herbicides. Glumate analogs, such as L-methionine-S-sulfoximine (MSO) and phosphonothricin (PPT), are effective herbicides. MSO and PPT may be herbicides acting not only through target enzymes, but also through GluR.

As shown in the working examples, infra the present invention also provides methods of screening and identifying novel plant growth regulators and pharmaceutical drugs that mimic or antagonize glutamate in regulating plant metabolism, physiology and/or gene expression. The novel plant growth regulators may have structural homology to agonists or antagonists of animal glutamate receptors. Such agonists and antagonists have uses as stimulatory or inhibiting plant growth regulators. Due to their structural homologies with animal glutamate receptors, plant glutamate receptors proteins and polypeptides can also be used in in vitro screening for drugs that act on animal glutamate receptors.

The methods of identifying these novel plant growth regulators are based on in vivo screening of chemicals for their abilities to alter plant growth, development or gene expression in a manner that can be reversed or enhanced by glutamate or glutamate-antagonists.

In other embodiments, the methods are based on in vitro screening of chemicals for their abilities to compete or interfere with glutamate binding of plant or animal GluR.

The present invention also encompasses the use of the cDNA clones of the plant GluR to not only select for new herbicides, but to also genetically engineer herbicide resistant plants. Given that glutamate acts as an important signal for growth and development, the invention also encompasses modulating the activity of the iGluR and mGluR to alter growth and development patterns of the plants by techniques such as transgenic plants. Therefore gene constructs encoding the plant glutamate receptor protein and polypeptides can be used in genetic engineering of plants to improve their agronomic or industrial properties.

5.1. THE PLANT GLUTAMATE RECEPTOR

The present invention encompasses the nucleotide coding sequence encoding plant GluR proteins and polypeptides. These nucleotide sequences were identified in Arabidopsis and shown to have homology to the animal glutamate receptor genes, iGluR and mGluR. Additional nucleotide sequences were identified in Arabidopsis as having a low degree of homology to the glutamate binding domain of the glutamate receptor, which are neither ionotropic nor metabotrobic, are also described herein. In a specific embodiment described herein, the plant GluR genes were identified by searching the Arabidopsis Expressed Sequence Taq (EST) databand (Newman et al., 1994, Plant Physiol. 106:1241–1255) for cDNAs with identity to the glutamate receptor of animals. The five EST clones that are identified in the present invention were not previously known to contain a high enough degree of homology to animal glutamate receptors to be identified as such in the Genebank. In the present invention the five EST clones were identified as potential glutamate receptors due to sequence homology and then further characterized as such as described below.

One Arabidopsis cDNA clone (EST#107M14T7, pAt-iGR-1) shares high identity to a class of glutamate receptors called ionotropic (iGluR) receptors which constitutes ligand-gated ion channels (Gasic and Hollmann, 1992, Annu. Rev. Physiol. 54:507–536; Kanai et al., 1993, TINS 16:365–370; O'Hara et al., 1993, Neuron 11:41–52; Seeburg, 1995, TINS 16:359–365). In animals, binding of glutamate to membrane bound iGluR stimulates the influx of Ca++ resulting in and fast excitatory neurotransmission which will subsequently cause a wide variety of downstream responses (Gasic and Hollmann, 1992, Annu. Rev. Physiol. 54:507–536; Kanai et al., 1993, TINS 16:365–370; O'Hara et al., 1993, Neuron 11:41–52; Seeburg, 1995, TINS 16:359–365).

A second Arabidopsis cDNA (EST#97C23T7, pAT-mGR-1) shares identity to another class of animal glutamate receptors called metabotropic glutamate receptor, mGluR (Gasic and Hollmann, 1992, Annu. Rev. Physiol. 54:507–536). In animals, the mGluR class of glutamate receptors is coupled to a G protein that is linked to inositol phosphate/diacylglycerol formation which results in subsequent release of calcium from internal stores (Gasic and Hollmann, 1992, Annu. Rev. Physiol. 54:507–536).

Three additional clones (EST#T20773, EST#ATT50711, EST#ATS2655) were identified in Arabidopsis as having a low degree of homology to the glutamate binding domain of the animal glutamate receptor. However, these clones do not correspond to ionotropic nor metabotropic animal GluRs. Therefore these clones may represent a novel class of glutamate-like receptors in plants. The plant GluR of the present invention span the plant cellular membrane, as well as intracellular membranes including vacuolar membranes, chloroplast membranes and mitochondrial membranes.

Figure 5:
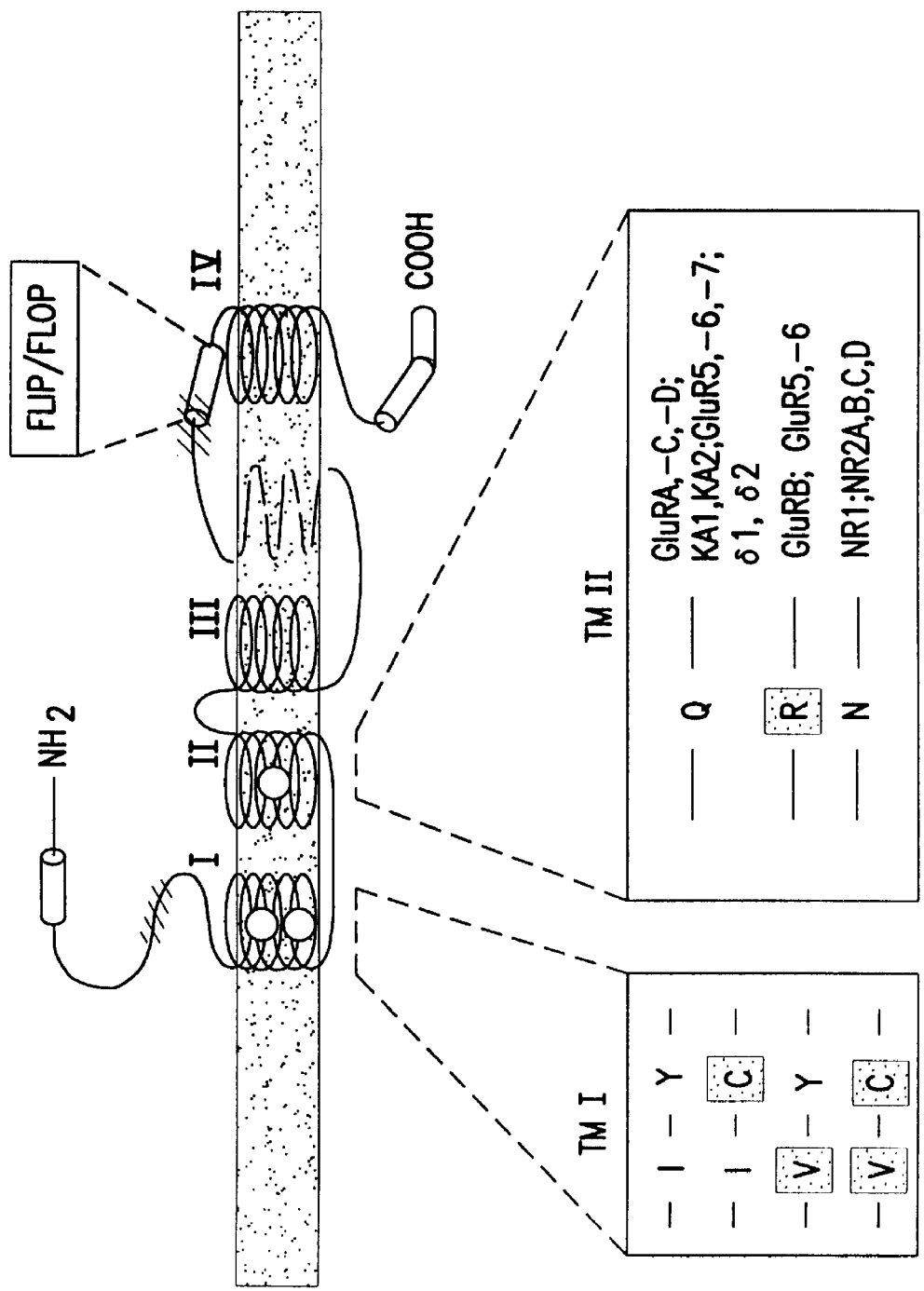

The Arabidopsis iGluR cDNA, pAt-iGR-1, shares extensive identity with animal iGluRs. The plant GluR is unique in that it has homology to both NMDA-type and KA-type GluR in animals. About 700 nucleotides from the 5' end of the clone pAt-iGR-1 have been sequenced. This clone encodes a truncated peptide which shares an extended region of homology with the ionotropic glutamate receptors which covers part of the glutamate-binding site close to transmembrane domain I (TMI) and continues through TMII until the end of TMIII (FIG. 5 and FIG. 7A). The highest identity to animal iGluR is in the glutamate-binding domain (52%) (FIG. 6). The glutamate-binding region of animal iGluR is a two cleft domain shown by the hatched bars in FIG. 5. The Arabidopsis sequence shown in FIG. 7B, corresponds to the first of these glutamate-binding domains in animal iGluR (FIG. 5). The glutamate-binding domain shared between animal and plant iGluR has low but significant identity to the glutamine-binding domain of an E. coli permease gene (Nakanishi et al., 1990, Neuron 5:569–581) (FIG. 6). The ligand-binding R residue, which is conversed in all ionotropic glutamate receptors, is also conserved in the putative Arabidopsis iGluR (Kuryatov et al., 1994, Neuron 12:1291–1300).

In non-NMDA type animal iGluRs (kainate-binding iGluR and AMPA iGluR), their mRNAs are subject to RNA editing which modifies their function. For example, in the GluR2 subunit in AMPA type iGluR, RNA editing (Q to R) in TM II (FIG. 1) has been shown to regulate the Ca++ permeability. RNA editing leads to a decrease in Ca++ permeability (Choi, 1988, Neuron 1:623–634; Hume et al., 1991, Science 253:1028–1031). In Kainate-Binding type iGluR, both the GluR5 and GluR6 subunits also display the Q to R editing similar to the case of GluR2 of AMPA receptors (Sommer et al., 1991, Cell 67:11–19). GluR6 has two additional positions in TMI that are modified by RNA editing (Kohler et al., 1993, Neuron 10:491–500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6(Q) channels (Kohler et al., 1993, Neuron 10:491–500). In the case of NMDA type iGluR, all of the subunits do not show RNA editing in TMI and TMII. In fact all subunits contain an N at the site which Q to R editing occurs. NMDA receptors are highly permeable to Ca++.

Interestingly, the Q/R residue of animal non-NMDA-type ionotropic glutamate receptor which are subject to RNA editing or the corresponding non-editing N residue of NMDA-type ionotropic glutamate receptor within TMII (Seeburg, 1995, TINS 16:359–365), are missing from the predicted peptide of Arabidopsis pAt-iGR-1. Since these residues are important for the regulation of permeability of Ca++ ions in animal ionotropic glutamate receptors (Burnashev et al., 1992, Neuron 8:189–198; Kohler et al., 1993, Neuron 10:491–500; Sommer et al., 1991, Cell 67:11–19) the Ca++ ion permeability in plant glutamate receptors may be regulated by a different mechanism.

The nucleotide sequences encoding Arabidopsis iGluR and mGluR genes can be used to screen cDNA libraries obtained from other plant species to identify further plant iGluR and GluR genes. A plant cDNA library may be screened, under conditions of reduced stringency, using a radioactively or nonradioactively labeled fragment of the Arabidopsis iGluR and mGluR clones. Alternatively, the Arabidopsis iGluR and mGluR sequences can be used to design degenerate or fully degenerate oligonucleotide probes which can be used as PCR probes or to screen plant cDNA libraries. Alternatively, the probes may be used to screen genomic libraries. As shown by working example, infra, this type of analysis has revealed the presence of both iGluR and mGluR genes in other dicots, such as tobacco, a legume, pea, and two monocots, corn and rice. For a review of cloning strategies which may be used, see e.g., Maniatis 1989 Molecular Cloning, A Laboratory Manual, Cold Spring Harbor Press, N.Y.

5.1.1. THE PLANT GluR CODING SEQUENCE

The plant glutamate receptor is a family of or class of receptors, including ionotropic and metabotropic glutamate receptors. The plant ionotropic glutamate receptor of the present invention has a binding site for glutamate comprising the following amino acid sequence (SEQ ID NO.1):
    Q R D K Y D A A V G D I T I T S N R S L Y V D - F T L P Y T D I G I G I L T V K K K The plant metabotropic glutamate receptor of the present invention contains a partial cysteine-rich region and spans part of the seven transmembrane domain, as shown in FIG. 7B. The plant GluR DNAs of the invention encompass any DNA molecule encoding a plant receptor which contains the amino acid sequence of the glutamate binding domain shown above. The cDNA sequences for a number of clones are shown in FIG. 7; in particular, a partial amino acid sequence of the Arabidopsis GluR is shown in FIG. 7A; a partial amino acid sequence of Arabidopsis mGluR is shown in FIG. 7B; and a partial cDNA sequence of other glutamate-like receptors (i.e., non-ionotropic and non-metabotropic) are shown in FIG. 7C.

As used herein, plant GluR DNA refers to (a) any DNA encoding a plant protein containing the amino acid sequence of the glutamate binding domain shown in FIG. 6; (b) any DNA encoding a plant protein containing the amino acid sequences shown in FIG. 7A, 7B and/or 7C; (c) any DNA sequence that hybridizes to the complement of the foregoing coding sequences under highly stringent conditions, e.g., hybridization to filter-bound DNA in 0.5M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or (d) any DNA sequence that hybridizes to the complement of the coding sequences disclosed herein under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as GluR gene antisense molecules, useful, for example, in gene regulation and/or as antisense primers in amplification reactions of GluR gene nucleic acid sequences. Further, such sequences may be used as part of ribozyme and/or triple helix sequences, also useful for GluR gene regulation. Still further, such molecules may be used as components of methods of screening and identifying novel plant growth regulators and pharmaceutical drugs that mimic or antagonize glutamate in binding to and activating glutamate receptors.

Fragments of the plant GluR DNA are also included within the scope of the invention. For example, DNA encoding a polypeptide or peptide corresponding to the glutamate binding domain may be useful for the expression of "soluble" plant GluRs. In a further embodiment of the invention, the plant GluR DNA or a modified sequence thereof may be ligated to a heterologous sequence to encode a fusion protein. For example, for screening peptide libraries it may be useful to encode a chimeric plant GluR protein expressing a heterologous epitope that is recognized by a commercially available antibody. A fusion protein may also be engineered to contain a cleavage site located between the plant GluR sequence and the heterologous protein sequence, so that the GluR can be cleaved away from the heterologous moiety. In another embodiment, DNA sequences encoding a fusion protein comprising all or a portion of the plant GluR protein fused to another protein with a desired activity are within the scope of the invention; e.g., enzymes such as GUS (β-glucuronidase), β-galactosidase, luciferase, etc.

In another embodiment, DNAs that encode mutant forms of the plant GluRs are also included within the scope of the invention. Such mutant plant GluR DNA sequences encompass deletions, additions and/or substitutions of nucleotide residues, or of regions coding for domains within the plant GluR protein. These mutated plant GluR DNAs may encode gene products that are functionally equivalent or which display properties very different from the native forms of plant GluR, as explained in Section 5.1.2. below.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells and/or plants that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

In addition to the gene sequences described above, homologues of such sequences, as may, for example, be present in other plant species may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated GluR gene sequence may be labeled and used to screen a cDNA library constructed from mRNA obtained from the organism of interest. The hybridization conditions used should be of a lower stringency when the cDNA library is derived from an organism different from the type of organism from which the labeled sequence was derived. Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, previously unknown GluR gene-type sequences may be isolated by performing PCR using two degenerate oligonucleotide primer pools designed on the basis of amino acid sequences within the gene of interest. The template for the reaction may be cDNA obtained by reverse transcription of mRNA prepared from cell lines or tissue known or suspected to express an GluR gene allele.

The PCR product may be subcloned and sequenced to ensure that the amplified sequences represent the sequences of an GluR gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the GluR gene identified is the normal, or wild type gene, this gene may be used to isolate mutant alleles of the gene. Mutant alleles may be isolated from plants either known or proposed to have a genotype which contributes abnormal growth characteristics. Mutant alleles and mutant allele products may then be utilized in the development of in vitro assays, plant assay systems, and transgenic plants as described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from plant cells, tissues or whole plants suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified and subjected to sequence analysis according to methods well known to those of skill in the art.

Additionally, an expression library can be constructed utilizing DNA isolated from or cDNA synthesized from plant cells, tissues or whole plants suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis according to methods well known to those of skill in the art.

5.1.2. PROTEIN PRODUCTS OF THE GluR GENE

The invention also encompasses GluR gene products encoded by nucleic acid sequences that hybridize to, and are therefore the complements of, the following DNA sequences: (a) any DNA sequence encoding a plant protein containing the amino acid sequence of the glutamate binding domain shown in FIG. 7; (b) any DNA encoding a plant protein containing the amino acid sequences shown in FIG. 7A, 7B and/or 7C; (c) any DNA sequence that hybridizes to the complement of the foregoing coding sequences under highly stringent conditions or less stringent conditions, as described in Section 5.1.1.

The amino acid sequence of the glutamate binding domain of the plant GluR is shown in FIG. 6. Partial amino acid sequences of various plant GluRs are shown in FIG. 7; in particular, the partial amino acid sequence of plant iGluR is shown in FIG. 7A; of plant mGluR is shown in FIG. 7B; and of other plant glutamate-like receptors are shown in FIG. 7C. Specifically, GluR gene products, sometimes referred to herein as "GluR proteins", may include GluR gene polypeptides or peptide fragments encoded by the plant GluR gene sequences.

The invention also encompasses peptide fragments of the plant GluR gene products. For example, polypeptides or peptides corresponding to the glutamate binding domain may be useful as "soluble" plant GluRs. Alternatively, peptides corresponding to the signaling domains of the plant GluR are also included in the scope of the invention. The plant GluR gene product or peptide fragments thereof, can be linked to a heterologous peptide or protein as a fusion protein. In addition, chimeric plant GluR expressing a heterologous epitope that is recognized by a commercially available antibody is also included in the invention. A durable fusion protein may also be engineered; i.e., a fusion protein which has a cleavage site located between the plant GluR sequence and the heterologous protein sequence, so that the plant GluR can be cleaved away from the heterologous moiety. For example, a collagenase cleavage recognition consensus sequence may be engineered between the GluR protein or peptide and the heterologous peptide or protein. The plant GluR domain can be released from this fusion protein by treatment with collagenase.

In addition, GluR gene products may include proteins that represent functionally equivalent gene products. Such equivalent GluR gene products may contain deletions, additions or substitutions of amino acid residues within the amino acid sequence encoded by the GluR gene sequences described, above, in Section 5.1.1., but which result in a silent change, thus producing a functionally equivalent GluR gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous GluR gene products encoded by the GluR gene sequences described in Section 5.1, above.

In an alternate embodiment, mutant GluR gene products can be designed or selected by mutational analysis in Arabidopsis, which demonstrate very different functions, including resistance to plant GluR antagonists that may be useful as herbicides. Such mutations encompass deletions, additions or substitutions of amino acid residues or the replacement of entire domains of the plant GluR to alter its functional activity. Alterations to either the glutamate binding domain, or the signaling domain of the plant GluR are encompassed by the invention. Alterations to the glutamate binding domain include exchanging portions of the binding domain with subunits from other glutamate receptors that bind specific agonists and antagonists. Also included in the invention is plant GluR gene products encoding proteins in which the glutamate binding domain has been exchanged for another ligand binding domain. Alterations to the signaling domain of the plant GluR include mutating potential phosphorylation sites and glycosylation sites on the receptor to alter its functional activity.

The GluR gene products may be produced by recombinant DNA technology using techniques well known in the art. Thus, methods for preparing the GluR gene polypeptides and peptides of the invention by expressing nucleic acid containing GluR gene sequences are described herein. Methods which are well known to those skilled in the art can be used to construct expression vectors containing GluR gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra.

In an alternate embodiment of the invention, the coding sequence of the plant GluR can be synthesized in whole or in part, using chemical methods well known in the art. See, for example, Caruthers, et al., 1980, Nuc. Acids Res. Symp. Ser. 7:215–233; Crea and Horn, 1980, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the plant GluR amino acid sequence in whole or in part. For example, peptides can be synthesized by solid phase techniques, cleaved from the resin and purified by high performance liquid chromatography. (E.g., see Creighton, 1983, Proteins, Structures and Molecular Principles, W. H. Freeman and Co., N.Y., pp. 50–60). The composition of the synthetic peptides may be confirmed by amino acid analysis or sequencing (e.g. the Edman degradation procedure; see Creighton, 1983, Proteins, Structures and Molecular Principles, W. H. Freeman and Co., N.Y. pp. 39–49).

5.2. EXPRESSION OF PLANT GluR AND GENERATION OF CELL LINES THAT EXPRESS THE PLANT GluR

In order to express a biologically active plant GluR, the nucleotide sequence coding for plant GluR or a functional equivalent as described in Section 5.1. supra, is inserted into an appropriate expression vector i.e. a vector which contains the necessary elements for transcription and translation of the inserted coding sequence. The plant GluR gene products as well as host cells or cell lines transfected or transformed with recombinant GluR expression vectors can be used for a variety of purposes.

In accordance with the invention, plant GluR nucleotide sequences which encode iGluR or mGluR, peptide fragments of plant iGluR and mGluR, iGluR and mGluR fusion proteins or functional equivalents thereof, may be used to generate recombinant DNA molecules that direct the expression of plant iGluR and mGluR proteins or a functional equivalent thereof in appropriate host cells. In addition, plant glutamate-like receptor sequences identified as having a low degree of homology to the glutamate binding domain may also be used to generate recombinant DNA molecules that direct the expression of non-iGluR, non-mGluR proteins with homology to glutamate binding domains or a functional equivalent thereof in appropriate host cells. Alternatively, nucleotide sequences which hybridize to portions of plant iGluR and mGluR sequences may also be used in nucleic hybridization assays, Southern and Northern blot analysis etc.

Due to the inherent degeneracy of the genetic code, other DNA sequences which encode substantially the same or a function equivalent amino acid sequence may be used in the practice of the invention for the cloning and expression of the plant GluR. Such DNA sequences include those which are capable of hybridizing to the plant iGluR and mGluR sequence under stringent conditions. DNA sequences also included in the invention are those sequences which bind under stringent conditions to the plant glutamate-like receptor sequences identified as having a low degree of homology to the glutamate binding domain.

Altered DNA sequences which may be used in accordance with the invention include deletions, additions or substitutions of different nucleotide residues resulting in a sequence that encodes the same or finally equivalent gene product. The gene product itself may contain deletions, additions or substitutions of amino acid residues within the plant iGluR and mGluR sequences. The DNA sequences of the invention may be engineered to alter the plant iGluR and mGluR sequences for a variety of ends including, but not limited to alterations which modify processing and expression of the gene product. For example, mutations may be introduced using techniques well known in the art, e.g. site-directed mutagenesis to insert new restriction sites, to alter glycosylation patterns, phosphorylation sites etc.

In another embodiment of the invention, the plant iGluR and mGluR sequence may be ligated to a heterologous sequence to encode a fusion protein. For example, for screening of peptide libraries it may be useful to encode a chimeric plant GluR protein expressing a heterologous epitope that is recognized by a commercially available antibody. A fusion protein may also be engineered to contain a cleavage site located between the plant GluR and the heterologous protein sequence, so that the GluR can be cleaved away from the heterologous moiety.

5.2.1. EXPRESSION SYSTEMS

Methods which are well known to those skilled in the art can be used to construct expression vectors containing the plant GluR coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the plant GluR coding sequence. These include but are not limited to microorganisms such as bacteria transformed with recombinant bacteriophage DNA, plasmid DNA or cosmid DNA expression vectors containing the plant GluR coding sequence; yeast transformed with recombinant yeast expression vectors containing the plant GluR coding sequence; insect cell systems infected with recombinant virus expression vectors (e.g., baculovirus) containing the plant GluR coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the plant GluR coding sequence; or animal cell systems infected with recombinant virus expression vectors (e.g., adenovirus, vaccinia virus) including cell lines engineered to contain multiple copies of the plant GluR either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the plant GluR DNA SV40-, BPV- and EBV-based vectors may be used with an appropriate selectable marker.

In bacterial systems a number of expression vectors may be advantageously selected depending upon the use intended for the plant GluR expressed. For example, when large quantities of plant GluR are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., 1983, EMBO J. 2:1791), in which the plant GluR coding sequence may be ligated into the vector in frame with the lac Z coding region so that a hybrid GluR lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the plant GluR coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

For long-term, high-yield production of recombinant proteins, stable expression is preferred. For example, cell lines which stably express the plant GluR may be engineered. Rather than using expression vectors which contain viral origins of replication, host cells can be transformed with the plant GluR DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the plant GluR on the cell surface, and which respond to glutamate mediated signal transduction. Such engineered cell lines are particularly useful in screening glutamate analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in $tk^-$, $hgprt^-$ or $aprt^-$ cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin genes (Santerre, et al., 1984, Gene 30:147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. IDENTIFICATION OF TRANSFECTANTS OR TRANSFORMANTS EXPRESSING THE PLANT GluR GENE PRODUCT

The host cells which contain the plant GluR coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of plant GluR mRNA transcripts in the host cell; and (d) detection of the gene product as measured by immunoassay or by its biological activity.

In the first approach, the presence of the plant GluR coding sequence inserted in the expression vector can be detected by DNA-DNA or DNA-RNA hybridization using probes comprising nucleotide sequences that are homologous to the plant GluR coding sequence or portions or derivatives thereof.

In the second approach, the recombinant expression vector/host system can be identified and selected based upon the presence or absence of certain "marker" gene functions (e.g., thymidine activity, resistance to antibiotics, resistance to methotrexate, transformation phenotype, occlusion body formation in baculovirus, etc.). For example, if the plant GluR coding sequence is within a marker gene sequence of the vector, recombinants containing the plant GluR coding sequence can be identified by the absence of the marker gene function. Alternatively, a marker gene can be placed in tandem with the plant GluR sequence under the control of the same or different promoter used to control the expression of the plant GluR coding sequence. Expression of the marker in response to induction or selection indicates expression of the plant GluR coding sequence.

In the third approach, transcriptional activity for the plant GluR coding region can be assessed by hybridization assays. For example, RNA can be isolated and analyzed by Northern blot using a probe homologous to the plant GluR coding sequence or particular portions thereof substantially as shown in FIGS. 6 and 7. Alternatively, total nucleic acids of the host cell may be extracted and assayed for hybridization to such probes.

In the fourth approach, the expression of the plant GluR protein product can be assessed immunologically, for example by Western blots, immunoassays such as radioimmuno-precipitation, enzyme-linked immunoassays and the like. The ultimate test of the success of the expression system, however, involves the detection of the biologically active plant GluR gene product. Where the host cell secretes the gene product, the cell free media obtained from the cultured transfectant host cell may be assayed for plant GluR activity. Where the gene product is not secreted, cell lysates may be assayed for such activity. In either case, a number of assays can be used to detect plant GluR activity including but not limited to the following: cyclooxygenase activity may be determined in the culture medium by the addition of exogenous arachidonic acid substrate (30 $\mu$M for 15 min. at 37° C.) followed by conversion of the prostayalandin $E_2$ product to a methyl oximate form. This bicyclic derivative may then be quantitated by radioimmunoassay (kit from Amersham Corp).

Desired plants and plant cells may be obtained by engineering the gene constructs described herein into a variety of plant cell types, including but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify a plant or plant cell transformant containing the gene constructs of the present invention. These methods include but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, also may be used to detect the presence or expression of the recombinant construct in specific plant organs and tissues. The methods for doing all these assays are well known to those skilled in the arts.

5.2.3. PURIFICATION OF THE PLANT GluR GENE PRODUCT

Once a cell that produces high levels of biologically active plant GluR is identified, the cell may be clonally expanded and used to produce large quantities of the receptor. The receptor may be purified using techniques well-known in the art including, but not limited to, immunoaffinity purification, chromatographic methods including high performance liquid chromatography and the like. Where the gene product is secreted by the cultured cells, plant GluR polypeptides or peptides may be readily recovered from the culture medium.

Where the plant GluR coding sequence has been engineered to encode a cleavable fusion protein, the purification of plant GluR may be readily accomplished using affinity purification techniques. For example, an antibody specific for the heterologous peptide or protein can be used to capture the durable fusion protein; for example, on a solid surface, a column etc. The plan GluR moiety can be released by treatment with the appropriate enzyme that cleaves the linkage site.

The ease of cDNA construction using the polymerase chain reaction, transfection and purification of the expressed protein permits the isolation of small, but sufficient amount of plant GluR for characterization of the receptor's physical and kinetic properties. Using site-directed mutagenesis or naturally occurring mutant sequences, this system provides a reasonable approach to determine the effects of the altered primary structure on the function of the protein. Fusion constructs having the domain of plant GluR preceding the amino terminus of the cleavable protein versus constructs having the opposite arrangement, may also be engineered to evaluate which fusion construct will interfere the least, if at all, with the protein's biologic function and the ability to be purified.

Using this aspect of the invention, any cleavage site or enzyme cleavage substrate may be engineered between the plant GluR sequence and a second peptide or protein that has a binding partner which could be used for purification, e.g, any antigen for which an immunoaffinity column can be prepared.

5.3. ANTIBODIES TO GluR PROTEINS

Antibodies that define the GluR gene product are within the scope of this invention, and include antibodies capable of specifically recognizing one or more GluR gene product epitopes. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of an GluR gene product in a biological sample, including, but not limited to, blood plasma and serum. Alternatively, the antibodies may be used as a method for the inhibition of abnormal GluR gene product activity.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against GluR gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. TRANSGENIC PLANTS THAT EXPRESS MUTANT GluR

Glutamate in plants may also act as an important signal for growth and development. It is therefore possible to alter the growth and development patterns of the plants by modulating the iGluR or mGluR or glutamate-like receptor activities by engineering transgenic plants express either wild type or mutant forms of plant GluR as discussed in Sections 5.1 and 5.2. Glutamate has potential activity in regulating circadium rythym, therefore it is possible to engineer transgenic plants expressing mutated GluR to alter the plant's response to light and the biological clock. Thus, for example it would be possible to engineer plants which flower early or later, etc. The overexpression of AS and GS genes results in plants with excellent growth traits, that is, they grow faster and larger. Therefore, it is possible by altering the GluR to stimulate expression of AS and GS genes, to genetically engineer plants with similar growth traits. In addition, by altering the GluR in genetically engineered cells it may also be possible to synchronize cells in culture, as well as synchronizing plants and seed germination.

According to the present invention, a desirable plant or plant cell may be obtained by transforming a plant cell with the nucleic acid constructs described in Section 5.1. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium can be employed to introduce the gene constructs into plants. Such transformations preferably use binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform as well as transfer DNA to monocotyledonous plants and plant cells. (see Hernalsteen et al., 1984, EMBO J 3:3039–3041 ; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

According to the present invention, a wide variety of plants and plant cell systems may be engineered for the desired physiological and agronomic characteristics described herein using the nucleic acid constructs of the instant invention and the various transformation methods mentioned above. In preferred embodiments, target plants and plant cells for engineering include, but are not limited to, those of maize, wheat, rice, soybean, tomato, tobacco, carrots, peanut, potato, sugar beets, sunflower, yam, Arabidopsis, rape seed, and petunia.

The present invention also encompasses the use of the cDNA clones of the plant GluR to not only select for new herbicides, but to also genetically engineer herbicide resistant plants. Gene constructs encoding the plant glutamate receptor protein and polypeptides can be used in genetic engineering of plants to alter the plant's growth requirements or conditions. The invention also encompasses genetically engineered plants that express mutagenized forms of the plant GluR so that the plants are able to utilize alternative nitrogen sources, which may prove to be beneficial, for example in improving plant growth in nitrogen limited soil. Given the important role that glutamate signaling plays in timing of cell division or flowering, transgenic plants may be engineered to produce more flowers or fruit in response to a specific nitrogen source. Therefore the present invention has many utilities in genetic engineering of plants to improve their agronomic or industrial properties.

The invention further encompasses transgenic plants expressing chimeric GluR. By exchanging portions of the glutamate binding domain with segments of receptors sensitive to other compounds it is possible to engineer a receptor with specific resistance or growth response to that specific compound. Animal GluR subunits with specificity to particular agonists have been identified. (Bach et al., 1994, Neuron 13:1343–1357). Through mutagenesis of the plant GluR it is possible to identify similar segments in plants and to genetically engineer GluR responsive to one specific agonist or analog of glutamate. Transgenic plants expressing such receptors would have improved agronomic and industrial properties.

5.5. SCREENING ASSAYS FOR HERBICIDES

The present invention also encompasses screening assays to identify agonists and antagonists of glutamate induced signaling. This invention provides a novel, rapid and cost effective means of screening or identifying novel plant growth regulators and pharmaceutical drugs. The methods are based in some cases on in vivo screening of drugs for their abilities to alter plant growth, development or gene expression in a manner that can be reversed or enhanced by glutamate or glutamate-antagonists. In other embodiments, the methods are based on in vitro screening of drugs for their abilities to compete or interfere with glutamate binding of plant or animal glutamate receptors. These methods may be used to identify novel stimulatory or inhibitory plant growth regulatory compounds.

5.5.1. IN VITRO ASSAYS

The present invention also encompasses the use of in vitro screens to identify drugs for their ability to interefere with glutamate binding of plant or animal glutamate receptors. A potential method for in vitro screening involves linking the isolated plant glutamate receptor to a solid matrix, such as a sepharose. A solution containing glutamate along with the specific drug in varying concentrations. After several washes, the amount of glutamate bound to the receptor can be measured by applying a radioactively or fluorescently tagged antibody directed to the glutamate binding domain. The effectiveness of the inhibitors would be measured by the amount of antibody in the flow through. This would be a very rapid and cost effective assay to initially screen for potential inhibitors of glutamate binding to its receptor.

5.5.2. CELL CULTURE ASSAYS

The present invention encompasses the use of cell lines, that express the plant GluR, in in vitro assays to screen drugs for their effects on plant growth mediated by the GluR. Preferably, continuous cell lines stably expressing the GluR gene product or mutants thereof as described above and preferably which respond to the signal generated by glutamate binding are utilized in assays to identify novel drugs that either mimic the effects of glutamate or act as glutamate antagonists. Cell lines that may be used in the cell culture assay include any cells, including animal, human or plant cells, that are engineered (as described in Section 5) to express the plant GluR. Glutamate receptor gene products encoding plant iGluR, mGluR, glutamate-like receptors, or any other glutamate receptor expressed in plants, as described in Section 5.1. may be expressed in cells for use in cell culture assay system.

In this assay, cells expressing the GluR in culture medium will be treated with potential agonists and antagonists. These drugs will be added in serial dilution to the culture medium. The effects of these drugs will be measured as changes in cell metabolism or growth, changes in gene expression, changes in downstream signaling events and changes in membrane potential. The effects of the drugs should be reversed by glutamate supplemention, which indicates that the inhibitory effects are specific to the glutamate-related process.

The cell culture assay will include cells expressing glutamate responsive gene promoters linked to reporter genes. AS and GS genes are induced in response to glutamate binding its receptor. Therefore, drugs can be tested for their ability to activate the GluR by induction of AS and GS genes. Induction of gene expression will be measured by linking the AS and GS promoters to reporter genes, such as chloramphenicol transferese, which are commonly used in the art. Induction of the GluR will be rapidly measured by assaying for the reporter genes activity.

The cell culture assay will also include assaying for GluR activators or inhibitors by measuring an electrophysiological response. Cells, i.e. Hela cells, expressing the plant GluR can be used to assay for inhibitors or activators of the GluR by measuring changes in membrane potential. Ionotropic GluR are known to be ion gated therefore activation or inhibition of the GluR may be measured as a change in membrane potential by methods well known to those skilled in the art.

The in vitro cell assay will provide a very rapid method to screen potential agonists and antagonists of the GluR. The use of cell lines expressing mutants of the GluR will provide more information regarding the action of these compounds. Primary cell cultures, protoplast and/or cell lines stably expressing the GluR which also express mutations in the signal transduction pathways will be a very useful tool in determining the downstream signaling events. For example, cell lines stably expressing the GluR may also express a mutant of the plant ras homolog or the plant mitogen-activated kinase (MAPK) homolog in order to determine whether ras or MAPK is required by glutamate mediated effects on cell metabolism and gene expression. Changes in MAPK activity or phosphorylation may also be utilized as an indicator of GluR activation.

This in vitro assay system is useful for screening and identifying potential inhibitors or activators of signaling cascades activated by plants. Cell lines expressing mutagenized GluR will provide a means of identifying inhibitors of GluR activated signaling events which may be potential herbicides. The effects or inhibitors or activators may be observed by measuring changes in gene expression and phosphorylation events by methods well known by those skilled in the art.

In another embodiment, the methods are based on in vitro screening of drugs for their abilities to compete or interfere with glutamate binding of animal glutamate receptors. Therefore the invention also encompasses plant cells expressing both wild-type and mutant forms of the animal GluR. In order to perform cell culture assays for drugs which would stimulate or inhibit animal glutamate receptors.

5.5.3. PLANT GROWTH ASSAY

In order to screen for potential plant growth regulators, assays measuring changes in plant growth in response to potential GluR agonists and antagonists in encompassed by the present invention. Assay measuring changes in plant growth include changes in root, stem, or leaf growth. The use of transgenic plants as described in Section 5.4. is also included.

The following assay may be utilized in order to screen drugs for their effects on plant growth mediated by the GluR. Arabidopsis seedlings expressing or overexpressing the GluR are treated with the potential agonist or antagonist. In this plant growth assay, Arabidopsis seeds are plated on tissue culture plates in MS Medium (Murashige and Skoog Salt Mixture-plant basic medium available from Gibco (BRL)). A dose-response curve is determined using various concentrations of the potential agonist or antagonist added to the medium. The plants are grown vertically in a growth chamber at 22° C. with a 16 hour light/8 hour dark cycle for two weeks. The effects of each herbicide on plant growth is assessed by measuring root length on vertical tissue culture plates. The effectiveness of the drug is measured by a increase or reduction in root growth. The effect of the drug should be reversed by glutamate supplementation, which indicates that the inhibitory effects are specific to a glutamate-related process.

This assay also has utility in the selection of new pharmacological agonists and antagonist for use as human drugs. The pathophysiological involvement of GluR receptors in animals has been reviewed (Gasic et al., 1992, Annu. Rev. Physiol. 54:507–536). As summarized by Gasic and Hollmann (1992), glutamate receptors in animals are involved in CNS disorders such as Huntington's disease, Parkinson's disease, and Alzheimer's disease. GluR is also involved in the initiation and propagation of seizures and in massive neuronal cell death during periods of ischemia and hypoglycemia. It has also been reported that NMDA receptor antagonists may confer protection to some neurotoxicity in an experimental model of Parkinson's disease (Graham et al. 1990, Life Sci 47:PL91–PL97). Moreover, both non-competitive NMDA receptor antagonist (dizocilpine) and competitive NMDA receptor antagonist (DlL-(E)-2-amino-4-methyl-5-phosphono-3-pentonoic acid) may act as antidepressant (Papp et al., 1994, Eur. J. Pharmacol. 263:1–7). Isolated Arabidopsis mutants which are supersensitive to GluR agonists or antagonists will be utilized to screen for new pharmaceutical drugs such as new antidepressants. The bioassay for new GluR acting drugs would be sensitive, rapid, and cost-effective to operate.

This assay will also have utility to screen and identify potential inhibitors or activators of signaling cascades activated by the plant GluR. The activation of the GluR leads to activation of downstream signaling events which are required for the observed changes in plant metabolism and development. Therefore the mutagenized Arabidopsis seedlings will have utility in assaying potential inhibitors or activators of the GluR activated signaling events. The effects of the inhibitors or activators will be observed by measuring changes in root length on vertical tissue plates.

5.6. HERBICIDES THAT BLOCK THE GluR SIGNAL

A further aspect of the invention relates to novel plant growth regulators that mimic or antagonize glutamate in regulating plant metabolism, physiology and/or gene expression. The novel plant growth regulators may have structural homology to agonists or antagonists of animal glutamate receptors. Plant growth regulators that mimic or antagonize the GluR may also be useful in synchronizing plant development and seed germination, as well as synchronizing cells in culture. The novel plant growth regulators may also have activities as agonists or antagonists of animal glutamate receptors.

Glutamate analogs should be effective herbicide targets, given that they are all acting not only through some target enzymes, but through plant amino acids receptors which signal downstream responses. The short-term and long-term herbicidal effects on the downstream reactions of these receptors would be more profound than the inhibition of a single biochemical reaction. The suggestion that some herbicides can affect a whole series of downstream responses have been implicated in Balke's review (Balke, 1985, In: Weed Physiology. CRC Press, Inc., p113–139). Several herbicides are suggested to be able to affect the hormonal and environmental regulation of membrane functions. For example, both the auxin and auxin antagonist herbicides affect membrane functions that are associated with the action of IAA in plant cells. Several herbicides can also affect the phytochrome-regulated Ca++ transport and blue light induced absorbance change. However, the detailed mechanisms of these herbicidal effects are yet to be fully elucidated and the corresponding receptors of the signals are poorly understood.

The present invention also includes plant growth regulators, including herbicides that prevent glutamate from binding to the glutamate receptor. Potential herbicides include, but are not limited to, peptides corresponding to extracellular domain of the glutamate receptor. These peptides would bind to glutamate and prevent binding to the receptor.

The present invention also includes herbicides that would not only act by binding to the GluR, but rather act intracellularly to inhibit downstream signaling pathways. Activation of the plant GluR results in the activation of signaling cascades. These signaling cascades and inhibitors thereof are well characterized in animals. Therefore given the strong identity between the animal and plant glutamate receptors, it is likely that similar signaling pathways are activated downstream and therefore inhibitors of these pathways in animal cells would have utility in plants. Therefore potential herbicides include, but are not limited to, inhibitors of plant homologues of ras, raf, protein tyrosine kinases, protein tyrosine phosphatases. Potential herbicides also include reagents which would inhibit intracellular activation of the glutamate receptor therefore blocking activation of downstream signaling cascades.

Herbicides which act via the GluR signaling pathway but are too large to cross the blood-brain barrier are especially preferred since they would be relatively non-toxic to humans and animals. For example, glutamate analogs such as PPT in theory should also be toxic to animals, as animals possess GS and glutamate receptors. However, PPT is not toxic to animals, as it does not pass the blood-brain barrier and effectively excreted in kidneys. This indicates that there may be plenty of room for constructing a herbicide which only affects plants but not animals. In addition, since the plant iGluR described herein appears to be "novel" in structure (combines kainate and NMDA domains), it is possibly distinct from those animal iGluRs and may be used to develop plant-specific herbicides.

In examples described below, glutamate is shown to induce the expression of a gene for asparagine synthetase (ASN1) in *Arabidopsis thaliana*. Thus, glutamate, an amino acid thought to be involved in nitrogen transport, can also act as a signaling molecule in plants. Arabidopsis cDNAs with high identity to a ionotropic animal glutamate receptor (iGluR) as well as one with high identity to animal metabotropic glutamate receptor (mGluR) are identified herein. The data described below shows that kainate, an iGluR agonist, can mimic the glutamate-stimulated induction of ASN1 mRNA. Conversely, an iGluR antagonist (DNQX) partially blocks the induction of ASN1 mRNA by glutamate. These data indicate that Arabidopsis possesses a functional iGluR.

6. EXAMPLE

IDENTIFICATION AND CHARACTERIZATION OF ARABIDOPSIS HOMOLOGS OF THE ANIMAL GLUTAMATE RECEPTOR GENE

Two Arabidopsis cDNA clones contained in the Arabidopsis Expressed Sequence Tag (EST) databank (Newman et al., 1994, Plant Physiol. 106:1241–1255). Two cDNA clones each with identity to a distinct type of animal glutamate receptor. One Arabidopsis cDNA clone (EST#107M14T7, pAt-iGR-1) shares high identity to a class of glutamate receptors called ionotropic (iGluR) receptors which constitutes ligand-gated ion channels (Gasic, G. P. and Hollmann, 1992, Annu. Rev. Physiol. 54:507–536; Kanai et al., 1993, TINS 16:365–370; O'Hara et al., 1993, Neuron 11:41–52; Seeburg, Ph.D., 1995, TINS 16:359–365. A second Arabidopsis cDNA (EST#97C23T7, pAT-mGR-1) shares identity to another class of animal glutamate receptors called metabotropic glutamate receptor, mGluR (Gasic, G. P. and Hollmann, 1992, Annu. Rev. Physiol. 54:507–536).

6.1. THE iGluR cDNA CLONE

Sequence analysis of each clone indicates that the Arabidopsis iGluR cDNA, pAt-iGR-1, shares extensive identity with animal iGluRs. About 700 nucleotides from the 5' end of the clone pAt-iGR-1 have been sequenced. This clone encodes a truncated peptide which shares an extended region of homology with the ionotropic glutamate receptor which cover part of the glutamate-binding site close to transmembrane domain I (TMI) and continues through TMII until the end of TMIII (FIG. 5 and FIG. 7A). The highest identity to animal iGluR is in the glutamate-binding domain (52%) (FIG. 6). The glutamate-binding region of animal iGluR is a two cleft domain shown by the hatched bars in FIG. 5. The Arabidopsis sequence shown in FIG. 6, corresponds to the first of these glutamate-binding domains in animal iGluR (FIG. 5). The glutamate-binding domain shared between animal and plant iGluR has low but significant identity to the glutamine-binding domain of an *E. coli* permease gene (Nakanishi et al., 1990, Neuron 5:569–581) (FIG. 6). The ligand-binding R residue, which is conserved in the Arabidopsis iGluR receptors, is also conserved in the Arabidopsis iGluR (Kuryatov et al., 1994, Neuron 12:1291–1300).

The mRNAs of non-NMDA type iGluRs (kainate-binding iGluR and AMPA iGluR) are subject to RNA editing which modifies their function. For example, in the GluR2 subunit in AMPA type iGluR, RNA editing (Q to R) in TM II (FIG. 1) has been shown to regulate the Ca++ permeability. RNA editing leads to a decrease in Ca++ permeability (Choi, D. W., 1988, Neuron 1:623–634; Hume et al., 1991, Science 253:1028–1031). In Kainate-binding type iGluR, both the GluR5 and GluR6 subunits display Q to R editing similar to that of the GluR2 subunit of AMPA receptors (Sommer et al., 1991, Cell 67:11–19). GluR6 has two additional positions in TMI that are modified by RNA editing (Kohler et al., 1993, Neuron 10:491–500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6 (Q) channels (Kohler et al., 1993, Neuron 10:491–500). In the case of NMDA type iGluR, all of the subunits do not show RNA editing in TMI and TMII. In fact all subunits contain an N at the site at which Q to R editing occurs. NMDA receptors are highly permeable to Ca++.

Interestingly, the Q/R residue of non-NMDA-type ionotropic glutamate receptor which are subject to RNA editing or the corresponding non-editing N residue of NMDA-type ionotropic glutamate receptor within TMII (Seeburg, P. H., 1995, TINS 16:359–365), are missing from the predicted peptide of Arabidopsis pAt-iGR-1. Since these residues are important for the regulation of permeability of Ca++ ions in animal ionotropic glutamate receptors (Burnashev et al., 1992, Neuron 8:189–198; Kohler et al., 1993, Neuron 10:491–500; Sommer et al., 1991, Cell 67:11–19) the Ca++ ion permeability in plant glutamate receptors may be regulated by a different mechanism.

Sequence searches of GeneBank data using FASTA program show that the peptide encoded by Arabidopsis pAt-iGR-1 has a strong homology to all of the kainate-binding, NMDA, and AMPA types of animal iGluRs, although it seems to have a slightly higher overall homology to kainate-binding type of iGluRs. FIG. 7A shows the extensive homology between the peptide encoded by the first 700 nucleotides of Arabidopsis pAt-iGR-1 to a NMDA and a kainate-binding iGluR (FIG. 7A). In contrast to animals which have distinct kainate and NMDA receptors, plants may possess a "novel" type of iGluR that combines domains of kainate and NMDA receptors.

Figure 8:
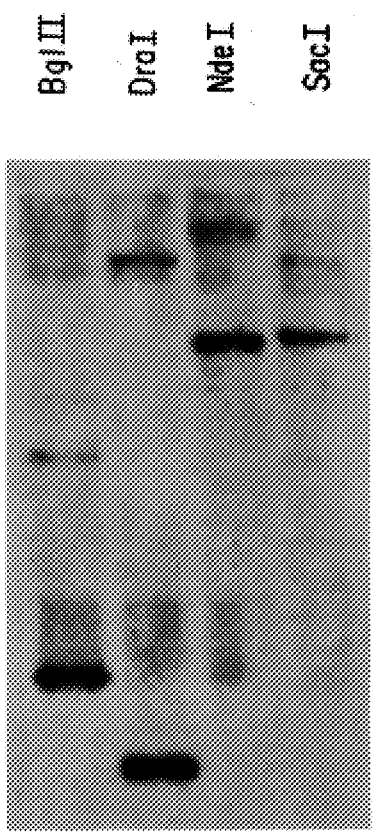
Figure 9:
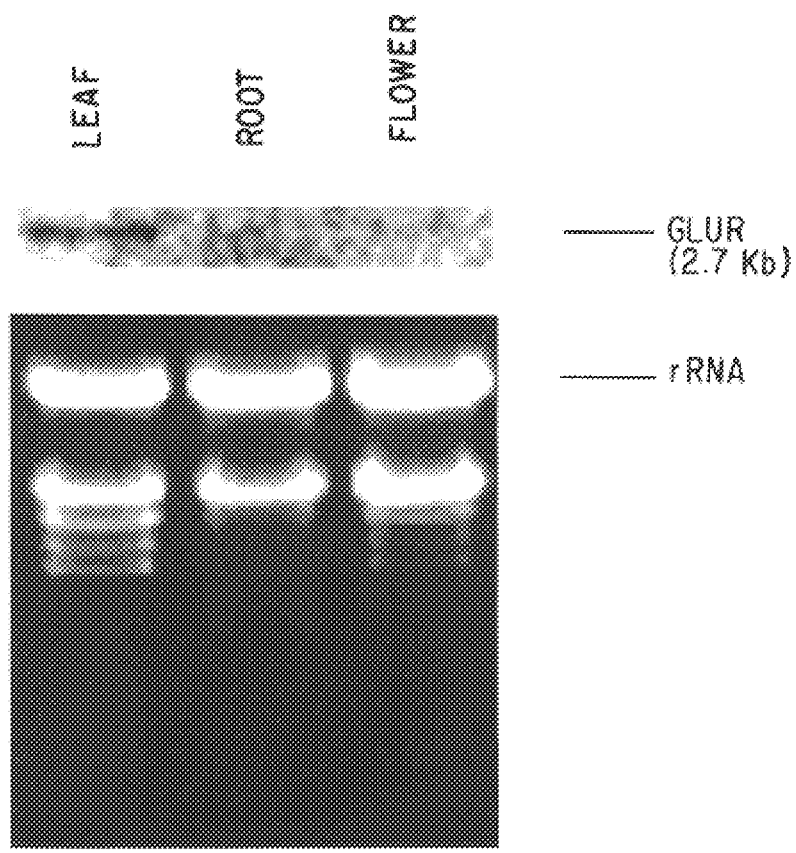

Northern blot analysis of leaf, root and flower tissues show that the iGluR mRNA is expressed at detectable levels (FIG. 9). In these experiments twenty μg of total RNA isolated from each of the leaf, root and flower tissues were electrophoresed on a 1% formaldehyde agarose gel. The Northern blot analyses were performed with high-stringency conditions at a temperature of 42° C. in 50% (v/v) formamide hybridization solution. Washing and chemiluminescent detection were performed according to the Boehringer-Mannheim Genius System User's Guide. This Northern shows iGluR mRNA is detected in 20 μg of total RNA. This Northern blot analysis also shows that Arabidopsis iGluR in RNA (2.7 Kb) is of comparable size to animal iGluR mRNA (3.0 Kb) (FIG. 8). The Arabidopsis iGluR mRNA is expressed predominantly in leaves and also at lower levels in roots and flowers of Arabidopsis.

6.2. THE mGluR cDNA CLONE

The Arabidopsis clone pAT-mGR-1 (EST #97C23T7) shares a high degree of homology to an animal mGluR as shown in FIG. 7B. The homologous region between Arabidopsis mGluR and animal mGluR includes part of the cysteine-rich region of animal mGluR and spans part of the 7 transmembrane domains (O'Hara et al., 1993, Neuron 11:41–52). In the Arabidopsis pAt-mGR-1 clone, there are several C residues in the cysteine-rich signature region as well (FIG. 7B).

Genomic Southern analyses demonstrate that the iGluR of Arabidopsis are bona-fide Arabidopsis genes as shown by the strongly hybridizing DNA fragments in Arabidopsis genomic DNA under high stringency condition (FIG. 8). The weakly hybridizing bands in each lane indicate that there may be additional GluR genes in the Arabidopsis genome. In these Southern blot analyses, two μg of CsCl-purified Arabidopsis genomic DNA was digested with different restriction enzymes. The digested DNA was electrophoresed on a 1% (w/v) Tris-phosphate-EDTA agarose gel. The DNA was transferred to a nylon membrane after depurination, denaturation and neutralization steps. Hybridization steps were carried out under high stringency conditions (65° C. in 0.5×SSC) or low stringency conditions (50° C. in 1×SSC).

Southern blot analyses using the Arabidopsis iGluR cDNAs on genomic DNA from other dicots (tobacco), a legume (pea), and two monocots (corn and rice) were performed under low-stringency conditions. This Southern blot analysis demonstrates that all plant species possess the iGluR genes described for Arabidopsis.

Genomic Southern blot analysis using Arabidopsis mGluR cDNA on genomic DNA from other dicots (tobacco), a legume (pea) and two monocots (corn and rice) were performed under low stringency conditions (50° C. in 1×SSC). The analysis demonstrated bands hybridizing to the mGluR in all species.

7. EXAMPLE

USE OF iGluR AGONIST (KA) AND ANTAGONIST (DNQX) TO DEFINE A FUNCTIONAL iGluR IN ARABIDOPSIS

The Arabidopsis iGluR cDNA (pAt-iGR-1) shows high identity to the animal glutamate receptors specifically activated by an iGluR agonist called kainic acid (KA). These kainate-selective iGluR receptors are competitively inhibited by an iGluR antagonist called 6,7-dinitroquinoxaline (DNQX). This iGluR agonist (KA) and antagonist (DNQX) are structurally distinct from glutamate (see FIG. 10), yet they bind to the iGluR receptor and stimulate or inhibit its action. Thus, any responses which these drugs may effect in plants, are likely to be due to their specific interaction with a iGluR-type receptor, rather than to general effects caused by inhibition of glutamate-utilizing enzymes. The experiments described below show that agonists, such as KA, mimic the effects of glutamate on gene induction and by contrast, that antagonists such as DNQX suppress glutamate gene induction. Thus, these experiments provide evidence that plants express a functional GluR.

7.1. EFFECT OF GluR AGONISTS AND ANTAGONISTS ON PLANT GROWTH

Figure 11A:
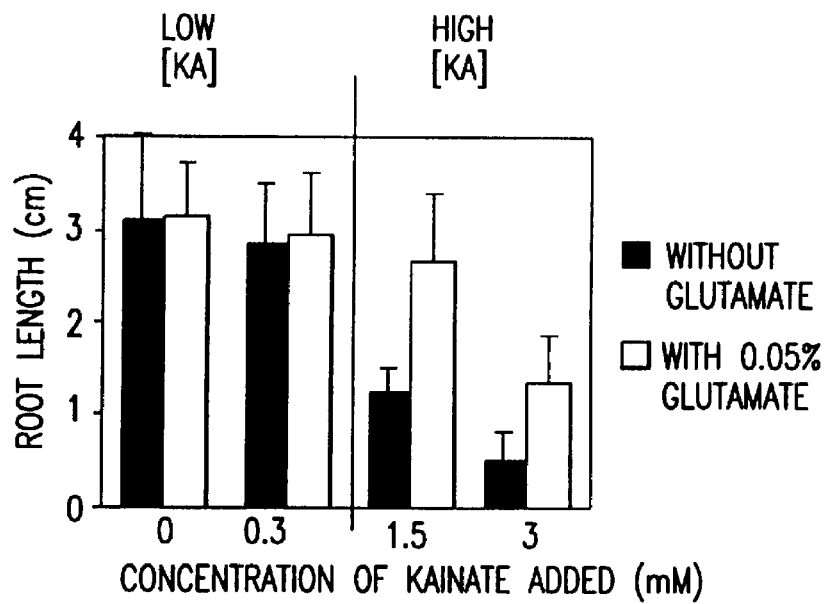
Figure 11B:
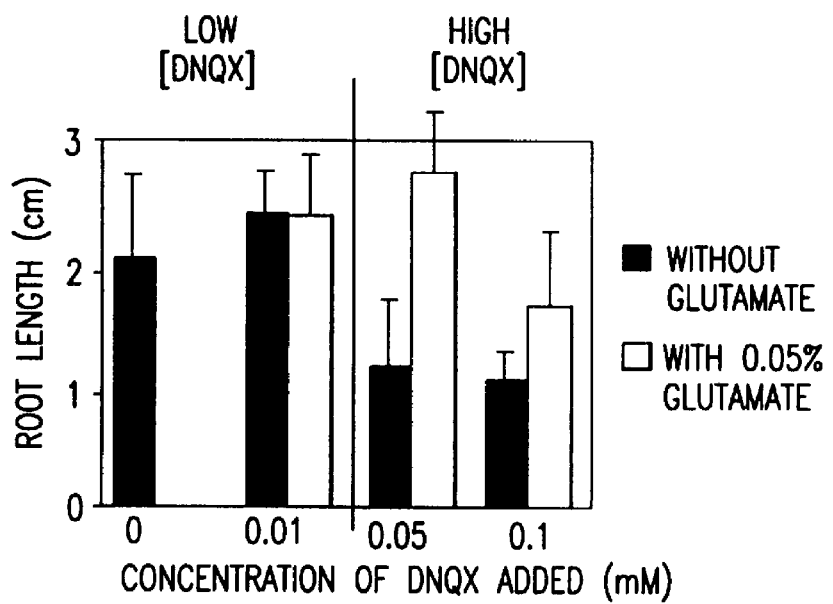
Figure 12A:
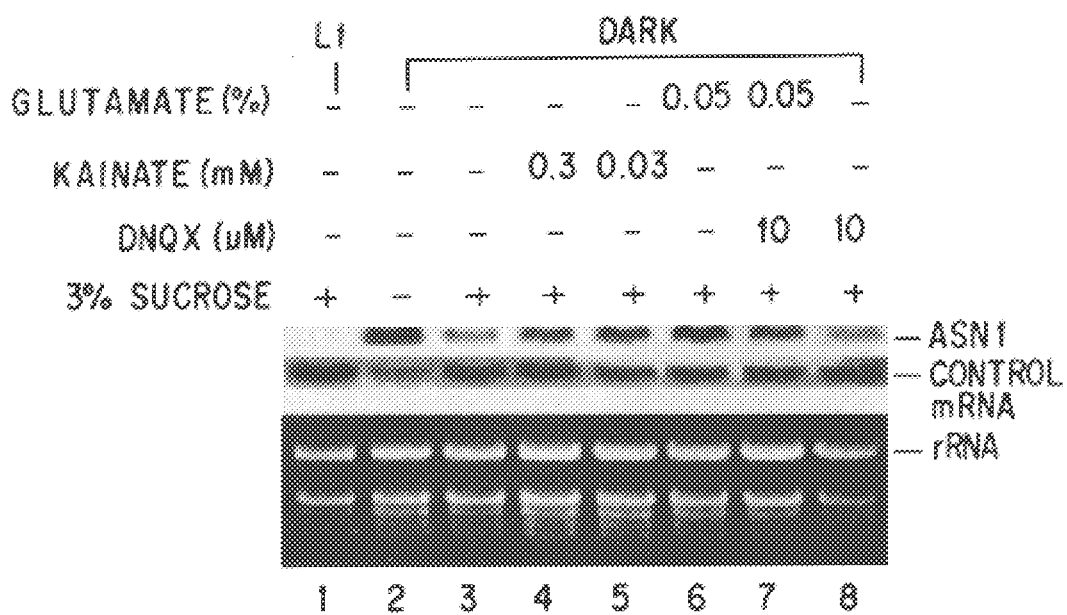

A dose-response curve using various concentrations of KA or DNQX was performed and the effects of each drug on plant growth was determined by measuring root length on vertical tissue culture plates (see FIG. 11). Low concentrations of agonist (KA) have no adverse effects on plant growth (FIG. 11A, left panel, compare 0 to 0.3 mM KA). Low concentrations of DNQX also have no adverse affects on growth (FIG. 11B, left panel, compare 0 to 0.01 mM DNQX). At high concentrations of agonist (KA) or antagonist (DNQX), a reduction in root growth is observed (FIG. 11A & B, right panels, black bars). In each case, the effect of high doses of KA or DNQX is at least partially reversed by glutamate supplementation (FIG. 12A &B, right panels, white bars). The partial rescue by glutamate indicates that the inhibitory effects of high KA or DNQX are specific to a glutamate-related process.

7.2. THE iGluR AGONIST (KA) IS ABLE TO INDUCE THE EXPRESSION OF PLANT NITROGEN-ASSIMILATORY GENES

The ability of a iGluR agonist to mimic the glutamate-stimulated expression of nitrogen assimilatory genes in Arabidopsis was tested using low concentrations of agonist KA and monitoring ASN1 mRNA levels as a measure of gene induction by KA. The results demonstrate that this iGluR agonist pair can specifically affect the expression of nitrogen metabolic genes in Arabidopsis. These data provide evidence that plants possess a functional glutamate receptor.

Figures 12B, 12C:
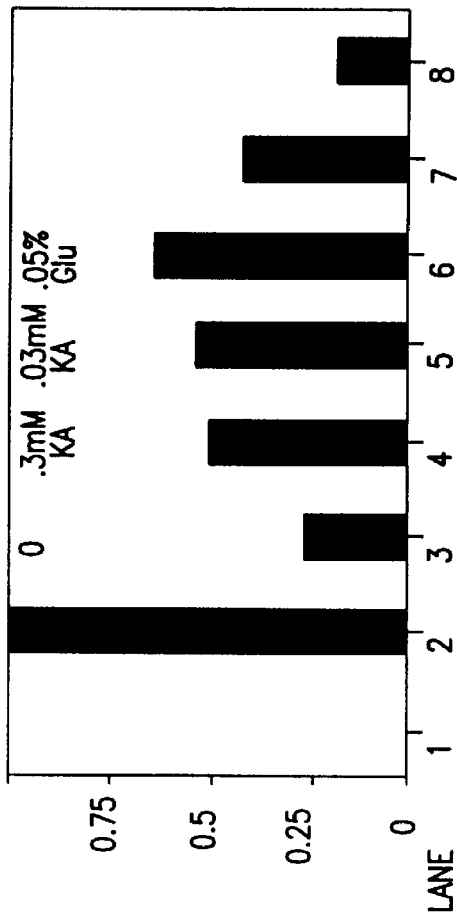
Figure 13A:
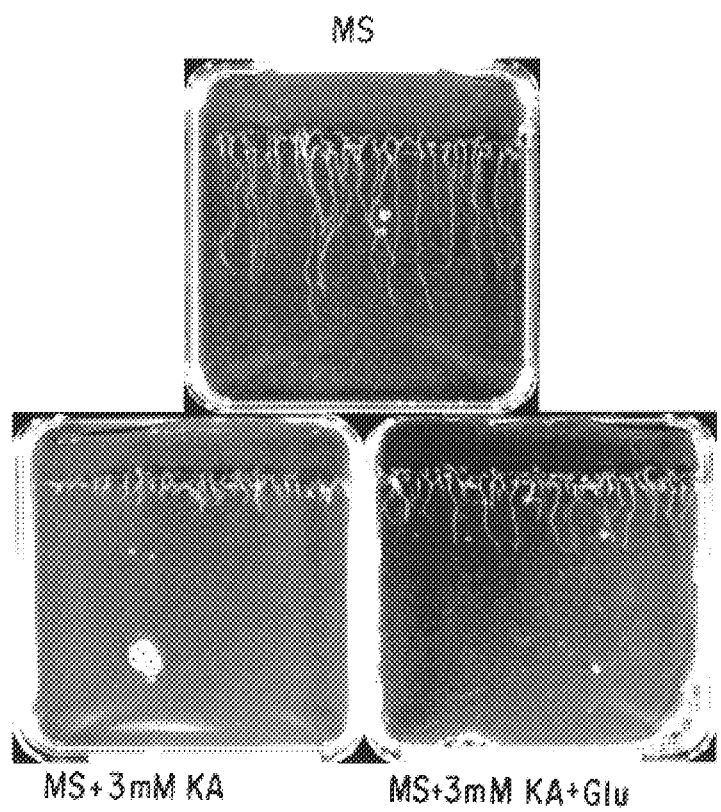
Figure 13B:
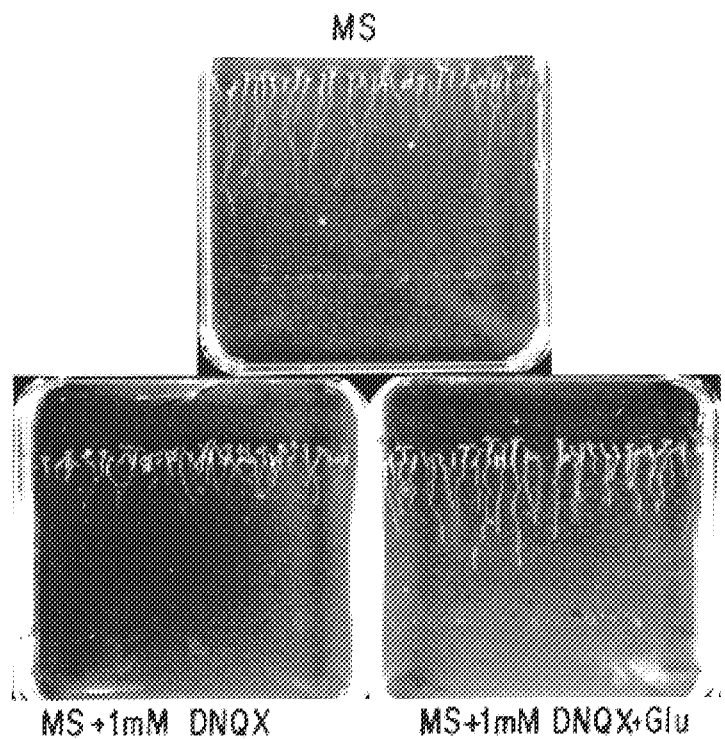

ASN1 mRNA accumulates to high levels specifically in dark-treated plants (FIG. 12A, lane 2), and is repressed by light (FIG. 12A, lane 1) or sucrose (FIG. 12A, lane 3). The results demonstrate that glutamate is able to partially relieve this sucrose repression (FIG., 12A, compare lane 6 to lane 3). Two concentrations of the iGluR agonist KA (300 μM and 30 μM) are each able to relieve the sucrose repression of ASN1 mRNA (FIG. 12A, lanes 4 & 5). ASN1 mRNA levels are determined by Northern blot analysis. FIG. 12B shows a quantitative bar graph of these Northern blot results. Quantitatively, KA and glutamate are each able to relieve the sucrose repression of ASN1 mRNA to nearly equivalent levels (FIG. 12C). This roughly 2-fold induction of ASN1 mRNA by KA or glutamate is comparable to the level of metabolic induction of several amino acid genes in yeast (2–4 fold) (Zalkin, H. and Yanofsky, C., 1982, J. Biol. Chem. 257:1491–1500). Conversely, the iGluR antagonist DNQX seems to partially inhibit glutamate-induction of ASN1 mRNA (FIG. 12A & B, compare lanes 6 & 7). The discovery that an iGluR agonist can mimic glutamate induction of a plant gene indicates that a functional iGluR glutamate receptor exists in plants.

7.3. LINKING THE ARABIDOPSIS iGluR GENE TO A FUNCTIONAL GLUTAMATE RECEPTOR IN PLANTS

The next experiments demonstrate that the iGluR gene(s) is responsible for the observed in vivo responses of ASN1 gene expression to iGluR agonist (KA) or iGluR antagonist (DNQX), using a genetic approach. Arabidopsis mutants are screened for insensitivity or supersensitivity to the iGluR agonist KA or antagonist DNQX. Arabidopsis mutants were selected in which a mutation in a iGluR gene may improve or disturb the binding affinity of the agonist or antagonist. In this assay, Arabidopsis seeds are plated on tissue culture plates in MS Medium (Murashige & Skoog Salt Mixture-plant basic medium available from Gibco (BRL). Agonists and antagonists are added in serial dilution to the medium. The plates are grown vertically in a growth chamber at 22° C. with a 16 hour light/8 hour dark cycle for two weeks. The effect of agonists and antagonists is determined by changes in root length. Mutagenized M2 Arabidopsis seedlings were screened for those which are insensitive (resistant) to the iGluR agonist (KA) or antagonist (DNQX) by screening for long roots on high concentrations of either drug (FIG. 15A).

Figure 14A:
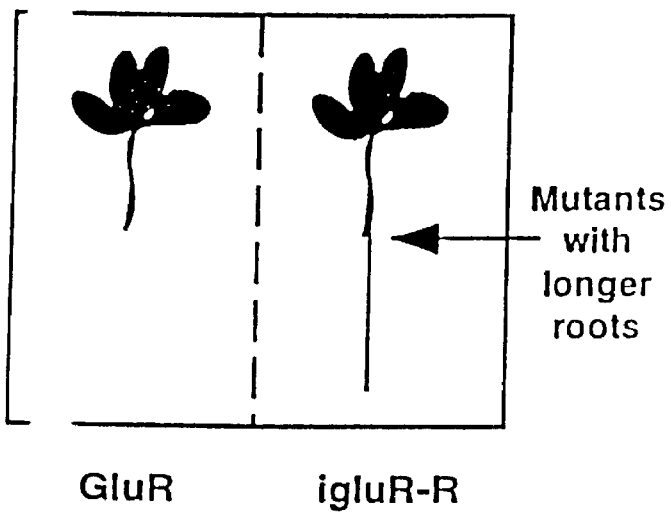
Figure 14B:
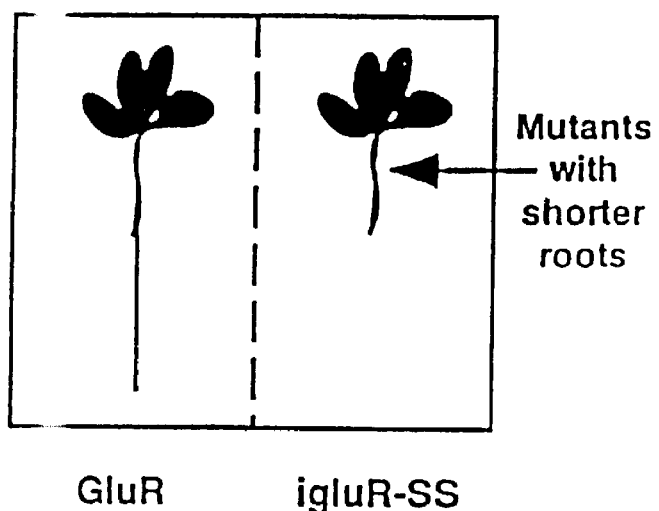

Conversely, mutants that are super-sensitive to either drug are being identified by screening for seedlings with short roots on low doses of KA or DNQX (FIG. 14B).

8. EXAMPLE

USE OF AGONISTS AND ANTAGONISTS TO DEFINE A FUNCTIONAL mGluR IN ARABIDOPSIS

The Arabidopsis mGluR cDNA (pAt-mGR-1) shows high identity to the animal glutamate receptors specifically activated by mGluR agonists called L-AP4 and ACPD. These mGluR receptors are specifically inhibited by mGluR antagonists L-AP3 (L-(+) amino phosphoropropionate) and L-ABHA (L-aspartate-B-hydroxymate). Any responses which these drugs may effect in plants are likely due to their specific interaction with an mGluR-type receptor, rather than to general effects caused by inhibition of glutamate-utilizing enzymes. In order to test that plants express a functional mGluR the assay described herein can be used, wherein agonists such as L-AP4 and ACPD will mimic the effects of glutamate on gene induction and by contrast antagonists such as L-AP3 and L-ABHA suppress glutamate gene induction. The effects of these agonists/antagonists can be tested using the vertical root growth assay as described in the working example, Section 7. Serial dilutions of the agonists/antagonists to be tested can range from 3 mM to 0 mM. In each case, the effects of doses of L-AP3, L-ABHA, L-AP4 and ACPD should be reversed by glutamate supplementation, indicating that the effect of these drugs are specific to glutamate related processes.

The present invention is not to be limited in scope by the specific embodiments described which are intended as single illustrations of individual aspects of the invention, and functionally equivalent methods and components are with in the scope of the invention. Indeed various modifications of the invention, in addition to those shown and described herein will become apparent to those skilled in the art from the foregoing description and accompanying drawings. Such modifications are intended to fall within the scope of the appended claims.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:1:

```
Gln  Arg  Asp  Lys  Tyr  Asp  Ala  Ala  Val  Gly  Asp  Ile  Thr  Ile  Thr  Ser
1                   5                             10                            15

Asn  Arg  Ser  Leu  Tyr  Val  Asp  Phe  Thr  Leu  Pro  Tyr  Thr  Asp  Ile  Gly
               20                       25                        30

Ile  Gly  Ile  Leu  Thr  Val  Lys  Lys  Lys
               35                       40
```

( 2 ) INFORMATION FOR SEQ ID NO:2:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:2:

```
Gln  Thr  Lys  Asn  Val  Asp  Leu  Ala  Leu  Ala  Gly  Ile  Thr  Ile  Thr  Asp
1                   5                             10                            15

Glu  Arg  Lys  Lys  Ala  Ile  Asp  Phe  Ser  Asp  Gly  Tyr  Tyr  Lys  Ser  Gly
               20                       25                        30

Leu  Leu  Val  Met  Val  Lys  Ala  Asn  Asn
               35                       40
```

(2) INFORMATION FOR SEQ ID NO:3:

(i) SEQUENCE CHARACTERISTICS:
    (A) LENGTH: 41 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:3:

```
Leu Arg Gln Glu Ala Asp Ile Ala Val Ala Pro Leu Thr Val Thr Ser
 1               5                  10                  15
Ala Arg Glu Glu Val Val Ser Phe Thr Pro Phe Leu Gln Thr Gly
            20                  25                  30
Ile Gly Ile Leu Leu Arg Lys Glu Thr
            35                  40
```

(2) INFORMATION FOR SEQ ID NO:4:

(i) SEQUENCE CHARACTERISTICS:
    (A) LENGTH: 41 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:4:

```
Ile Arg Lys Glu Ala Asp Leu Ala Ile Ala Pro Leu Thr Ile Thr Ser
 1               5                  10                  15
Val Arg Glu Asn Ala Ile Ser Phe Thr Lys Pro Phe Met Gln Thr Gly
            20                  25                  30
Ile Gly Ile Leu Leu Lys Lys Asp Thr
            35                  40
```

(2) INFORMATION FOR SEQ ID NO:5:

(i) SEQUENCE CHARACTERISTICS:
    (A) LENGTH: 41 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:5:

```
Val Tyr Gly Arg Ala Asp Val Ala Val Ala Pro Leu Thr Ile Thr Leu
 1               5                  10                  15
Val Arg Glu Glu Val Ile Asp Phe Ser Lys Pro Phe Met Ser Leu Gly
            20                  25                  30
Ile Ser Ile Met Ile Lys Lys Pro Gln
            35                  40
```

(2) INFORMATION FOR SEQ ID NO:6:

(i) SEQUENCE CHARACTERISTICS:
    (A) LENGTH: 41 amino acids
    (B) TYPE: amino acid
    (C) STRANDEDNESS:
    (D) TOPOLOGY: unknown (ii) MOLECULE TYPE: peptide (xi) SEQUENCE DESCRIPTION: SEQ ID NO:6:

```
Val Tyr Gly Arg Ala Asp Ile Ala Val Ala Pro Leu Thr Ile Thr Leu
 1               5                  10                  15
```

```
        Val  Arg  Glu  Glu  Val  Ile  Asp  Phe  Ser  Lys  Pro  Phe  Met  Ser  Leu  Gly
                       20                       25                       30

Ile  Ser  Ile  Met  Ile  Lys  Lys  Pro  Gln
                       35                       40
```

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:7:

```
        Val  Tyr  Gly  Lys  Ala  Asp  Ile  Ala  Ile  Ala  Pro  Leu  Thr  Ile  Thr  Leu
        1                   5                        10                       15

Val  Arg  Glu  Glu  Val  Ile  Asp  Phe  Ser  Lys  Pro  Phe  Met  Ser  Leu  Gly
                       20                       25                       30

Ile  Ser  Ile  Met  Ile  Lys  Lys  Pro  Gln
                       35                       40
```

( 2 ) INFORMATION FOR SEQ ID NO:8:

( i ) SEQUENCE CHARACTERISTICS:
        ( A ) LENGTH: 262 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:8:

```
        Arg  Gly  Asn  Asn  Asp  Asn  Leu  Ala  Tyr  Leu  Leu  Ser  Thr  Gln  Arg  Asp
        1                   5                        10                       15

Lys  Tyr  Asp  Ala  Ala  Val  Gly  Asp  Ile  Thr  Ile  Thr  Ser  Asn  Arg  Ser
                       20                       25                       30

Leu  Tyr  Val  Asp  Phe  Thr  Leu  Pro  Tyr  Thr  Asp  Ile  Gly  Ile  Gly  Ile
                       35                       40                       45

Leu  Thr  Val  Lys  Lys  Lys  Ser  Gln  Gly  Met  Trp  Thr  Phe  Phe  Asp  Pro
                  50                       55                       60

Phe  Glu  Lys  Ser  Leu  Trp  Leu  Ala  Ser  Gly  Ala  Phe  Phe  Val  Leu  Thr
        65                       70                       75                        80

Gly  Ile  Val  Val  Trp  Leu  Val  Glu  Arg  Pro  Val  Asn  Pro  Glu  Phe  Gln
                            85                       90                       95

Gly  Ser  Trp  Gly  Gln  Gln  Leu  Ser  Met  Met  Leu  Leu  Val  Trp  Ile  Leu
                       100                      105                      110

Leu  Pro  Leu  Cys  Leu  Leu  Thr  Gly  Glu  Lys  Leu  Gln  Lys  Met  Ser  Ser
                       115                      120                      125

Arg  Phe  Leu  Val  Ile  Val  Trp  Val  Phe  Val  Val  Leu  Ile  Leu  Thr  Ser
                  130                      135                      140

Ser  Tyr  Ser  Ala  Asn  Leu  Thr  Ser  Thr  Lys  Thr  Ile  Ser  Arg  Met  Gln
        145                      150                      155                      160

Leu  Asn  His  Gln  Met  Val  Phe  Gly  Gly  Ser  Thr  Thr  Ser  Met  Thr  Ala
                            165                      170                      175

Lys  Leu  Gly  Ser  Ile  Asn  Gly  Gly  Gly  Leu  Cys  Thr  Thr  Leu  Arg
                       180                      185                      190

Asp  Gly  Thr  Leu  Thr  His  Val  Ile  Asn  Glu  Ile  Pro  Tyr  Leu  Ser  Ile
                       195                      200                      205
```

5,824,867

Leu    Ile    Gly    Asn    Tyr    Pro    Asn    Asp    Phe    Val    Met    Thr    Asp    Arg    Val    Thr
                       210                         215                                256    220

Asn    Thr    Asn    Gly    Phe    Gly    Phe    Met    Phe    Gln    Lys    Gly    Ser    Asp    Leu    Val
                225                                230                         235                                       240

Pro    Lys    Val    Ser    Arg    Glu    Ile    Ala    Lys    Leu    Arg    Ser    Leu    Gly    Met    Leu
                                            245                                250                                255

Lys    Asp    Met    Glu    Glu    Lys
                                     260

( 2 ) INFORMATION FOR SEQ ID NO:9:

( i ) SEQUENCE CHARACTERISTICS:
        ( A ) LENGTH: 295 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:9:

Tyr    Leu    Val    Thr    Asn    Gly    Lys    His    Gly    Lys    Lys    Val    Asn    Asn    Val    Trp
                1                            5                                  10                                       15

Asn    Gly    Met    Ile    Gly    Glu    Val    Val    Tyr    Gln    Arg    Ala    Val    Met    Ala    Val
                                     20                         25                                 30

Gly    Ser    Leu    Thr    Ile    Asn    Glu    Glu    Arg    Ser    Glu    Val    Val    Asp    Phe    Ser
                                     35                         40                                 45

Val    Pro    Phe    Val    Glu    Thr    Gly    Ile    Ser    Val    Met    Val    Ser    Arg    Ser    Asn
                       50                                 55                                 60

Gly    Thr    Val    Ser    Pro    Ser    Ala    Phe    Leu    Glu    Pro    Phe    Ser    Ala    Ser    Val
                65                                 70                                 75                                 80

Trp    Val    Met    Met    Phe    Val    Met    Leu    Leu    Ile    Val    Ser    Ala    Ile    Ala    Val
                                            85                                 90                                 95

Phe    Val    Phe    Glu    Tyr    Phe    Ser    Pro    Val    Gly    Tyr    Asn    Arg    Asn    Leu    Ala
                                     100                        105                                110

Lys    Gly    Lys    Ala    Pro    His    Gly    Pro    Ser    Phe    Thr    Ile    Gly    Lys    Ala    Ile
                              115                               120                                125

Trp    Leu    Leu    Trp    Gly    Leu    Val    Phe    Asn    Asn    Ser    Val    Pro    Val    Gln    Asn
                       130                               135                                140

Pro    Lys    Gly    Thr    Thr    Ser    Lys    Ile    Met    Val    Ser    Val    Trp    Ala    Phe    Phe
                145                               150                                155                               160

Ala    Val    Ile    Phe    Leu    Ala    Ser    Tyr    Thr    Ala    Asn    Leu    Ala    Ala    Phe    Met
                                            165                               170                                175

Ile    Gln    Glu    Glu    Phe    Val    Asp    Gln    Val    Thr    Gly    Leu    Ser    Asp    Lys    Lys
                                     180                               185                                190

Phe    Gln    Arg    Pro    His    Asp    Tyr    Ser    Pro    Pro    Phe    Arg    Phe    Gly    Thr    Val
                              195                               200                                205

Pro    Asn    Gly    Ser    Thr    Glu    Arg    Asn    Ile    Arg    Asn    Asn    Tyr    Pro    Tyr    Met
                       210                               215                                220

His    Gln    Tyr    Met    Thr    Lys    Phe    Asn    Gln    Lys    Gly    Val    Glu    Asp    Ala    Leu
                225                               230                                235                               240

Val    Ser    Leu    Lys    Thr    Gly    Lys    Leu    Asp    Ala    Phe    Ile    Tyr    Asp    Ala    Ala
                                            245                               250                                255

Val    Leu    Asn    Tyr    Lys    Ala    Gly    Arg    Asp    Glu    Gly    Cys    Lys    Leu    Val    Thr
                                     260                               265                                270

Ile    Gly    Ser    Gly    Tyr    Ile    Phe    Ala    Thr    Thr    Gly    Tyr    Gly    Ile    Ala    Leu
                              275                               280                                285

```
            Gln  Lys  Gly  Ser  Pro  Trp  Lys
                 290                      295
```

( 2 ) INFORMATION FOR SEQ ID NO:10:

( i ) SEQUENCE CHARACTERISTICS:
        ( A ) LENGTH: 297 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:10:

```
Ser  Tyr  Glu  Ile  Arg  Leu  Val  Glu  Asp  Gly  Lys  Tyr  Gly  Ala  Gln  Asp
  1              5                    10                        15

Asp  Lys  Gly  Gln  Trp  Asn  Gly  Met  Val  Lys  Glu  Leu  Ile  Asp  His  Lys
              20                    25                        30

Ala  Asp  Leu  Ala  Val  Ala  Pro  Leu  Thr  Ile  Thr  His  Val  Arg  Glu  Lys
         35                        40                        45

Ala  Ile  Asp  Phe  Ser  Lys  Pro  Phe  Met  Thr  Leu  Gly  Val  Ser  Ile  Leu
     50                        55                        60

Tyr  Arg  Lys  Pro  Asn  Gly  Thr  Asn  Pro  Ser  Val  Phe  Ser  Phe  Leu  Asn
 65                        70                        75                        80

Pro  Leu  Ser  Pro  Asp  Ile  Trp  Met  Tyr  Val  Leu  Leu  Ala  Tyr  Leu  Gly
                85                        90                        95

Val  Ser  Cys  Val  Leu  Phe  Val  Ile  Ala  Arg  Phe  Ser  Pro  Tyr  Glu  Trp
               100                       105                       110

Tyr  Asp  Ala  His  Pro  Cys  Asn  Pro  Gly  Ser  Glu  Val  Val  Glu  Asn  Asn
               115                       120                       125

Phe  Thr  Leu  Leu  Asn  Ser  Phe  Trp  Phe  Gly  Met  Gly  Ser  Leu  Met  Gln
     130                       135                       140

Gln  Gly  Ser  Glu  Leu  Met  Pro  Lys  Ala  Leu  Ser  Thr  Arg  Ile  Ile  Gly
145                       150                       155                       160

Gly  Ile  Trp  Trp  Phe  Phe  Thr  Leu  Ile  Ile  Ile  Ser  Ser  Tyr  Thr  Ala
               165                       170                       175

Asn  Leu  Ala  Ala  Phe  Leu  Thr  Val  Glu  Arg  Met  Glu  Ser  Pro  Ile  Asp
               180                       185                       190

Ser  Ala  Asp  Asp  Leu  Ala  Lys  Gln  Thr  Lys  Ile  Glu  Tyr  Gly  Ala  Val
          195                       200                       205

Lys  Asp  Gly  Ala  Thr  Met  Thr  Phe  Phe  Lys  Lys  Ser  Lys  Ile  Ser  Thr
          210                       215                       220

Phe  Glu  Lys  Met  Trp  Ala  Phe  Met  Ser  Ser  Lys  Pro  Ser  Ala  Leu  Val
225                       230                       235                       240

Lys  Asn  Asn  Glu  Glu  Gly  Ile  Gln  Arg  Thr  Leu  Thr  Ala  Asp  Tyr  Ala
                    245                       250                       255

Leu  Leu  Met  Glu  Ser  Thr  Thr  Ile  Glu  Tyr  Ile  Thr  Gln  Arg  Asn  Cys
               260                       265                       270

Asn  Leu  Thr  Gln  Ile  Gly  Gly  Leu  Ile  Asp  Ser  Lys  Gly  Tyr  Gly  Ile
          275                       280                       285

Gly  Thr  Pro  Met  Gly  Ser  Pro  Tyr  Arg
     290                       295
```

( 2 ) INFORMATION FOR SEQ ID NO:11:

( i ) SEQUENCE CHARACTERISTICS:
        ( A ) LENGTH: 179 amino acids
        ( B ) TYPE: amino acid
        ( C ) STRANDEDNESS:

(D) TOPOLOGY: unknown (ii) MOLECULE TYPE: protein (xi) SEQUENCE DESCRIPTION: SEQ ID NO:11:

| Gly | Lys | Gly | Val | Arg | Glu | Ile | Pro | Ser | Ser | Val | Cys | Thr | Leu | Pro | Cys |
|---|---|---|---|---|---|---|---|---|---|---|---|---|---|---|---|
| 1 | | | | 5 | | | | | 10 | | | | | 15 | |
| Lys | Pro | Gly | Gln | Arg | Lys | Lys | Thr | Gln | Lys | Gly | Thr | Pro | Cys | Cys | Trp |
| | | | 20 | | | | 25 | | | | | 30 | | | |
| Thr | Cys | Glu | Pro | Cys | Asp | Gly | Tyr | Gln | Tyr | Gln | Phe | Asp | Glu | Met | Thr |
| | | 35 | | | | 40 | | | | | 45 | | | | |
| Cys | Gln | His | Cys | Pro | Tyr | Asp | Gln | Arg | Pro | Asn | Glu | Asn | Arg | Thr | Gly |
| | 50 | | | | 55 | | | | | 60 | | | | | |
| Cys | Gln | Asn | Ile | Pro | Ile | Ile | Lys | Leu | Glu | Trp | His | Ser | Pro | Trp | Ala |
| 65 | | | | 70 | | | | | 75 | | | | | 80 | |
| Val | Ile | Pro | Val | Phe | Leu | Ala | Met | Leu | Gly | Ile | Ile | Ala | Thr | Ile | Phe |
| | | | | 85 | | | | | 90 | | | | | 95 | |
| Val | Met | Ala | Thr | Phe | Ile | Arg | Tyr | Asn | Asp | Thr | Pro | Ile | Val | Arg | Ala |
| | | | 100 | | | | | 105 | | | | | 110 | | |
| Ser | Gly | Arg | Glu | Leu | Ser | Tyr | Val | Leu | Leu | Thr | Gly | Ile | Phe | Leu | Cys |
| | | 115 | | | | | 120 | | | | | 125 | | | |
| Tyr | Ile | Ile | Thr | Phe | Leu | Met | Ile | Ala | Lys | Pro | Asp | Val | Ala | Val | Cys |
| | 130 | | | | | 135 | | | | | 140 | | | | |
| Ser | Phe | Arg | Arg | Val | Phe | Leu | Gly | Leu | Gly | Met | Cys | Ile | Ser | Tyr | Ala |
| 145 | | | | | 150 | | | | | 155 | | | | | 160 |
| Ala | Leu | Leu | Thr | Lys | Thr | Asn | Arg | Ile | Tyr | Arg | Ile | Phe | Glu | Gln | Gly |
| | | | | 165 | | | | | 170 | | | | | 175 | |
| Lys | Lys | Ser | | | | | | | | | | | | | |

(2) INFORMATION FOR SEQ ID NO:12:

(i) SEQUENCE CHARACTERISTICS:
(A) LENGTH: 115 amino acids
(B) TYPE: amino acid
(C) STRANDEDNESS:
(D) TOPOLOGY: unknown (ii) MOLECULE TYPE: protein (xi) SEQUENCE DESCRIPTION: SEQ ID NO:12:

| Thr | Phe | Xaa | Cys | Trp | Leu | Lys | Asn | Ala | Phe | Cys | Ala | Ser | Ser | Phe | Phe |
|---|---|---|---|---|---|---|---|---|---|---|---|---|---|---|---|
| 1 | | | | 5 | | | | | 10 | | | | | 15 | |
| Gln | Leu | Ser | Ser | Met | Glu | Pro | Tyr | Arg | Leu | Arg | Leu | Arg | Phe | Ser | Phe |
| | | | 20 | | | | 25 | | | | | 30 | | | |
| Gln | Lys | Cys | Ser | Ile | Ala | Ala | Phe | Leu | Gly | Pro | Ala | Val | Ser | Phe | Asn |
| | | 35 | | | | 40 | | | | | 45 | | | | |
| Ser | Ile | Glu | Arg | Phe | Leu | Asn | Ser | Leu | Ser | Thr | Ser | Leu | Ile | Phe | Val |
| | 50 | | | | 55 | | | | | 60 | | | | | |
| Xaa | Phe | Ser | Ser | Met | Tyr | Phe | Leu | Ser | Xaa | Thr | Cys | Ser | Ser | Ser | Ile |
| 65 | | | | 70 | | | | | 75 | | | | | 80 | |
| Ile | Phe | Ser | Val | Xaa | Val | Ile | Thr | Gly | Ala | Phe | Leu | Ala | Arg | Pro | Ser |
| | | | | 85 | | | | | 90 | | | | | 95 | |
| Ala | Pro | Ile | Ser | Ala | Phe | Ser | Phe | Gly | Ser | Asp | Ala | Ile | Ile | Ser | Phe |
| | | | 100 | | | | | 105 | | | | | 110 | | |
| Ser | Leu | Lys | | | | | | | | | | | | | |
| | | 115 | | | | | | | | | | | | | |

(2) INFORMATION FOR SEQ ID NO:13:

(i) SEQUENCE CHARACTERISTICS:
    (A) LENGTH: 235 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:13:

| | | | | | |
|---|---|---|---|---|---|
| TGAAGATGCA | GGACAGGTTC | AATGGAGGTA | TGATAACCCT | CCAGACTTCA | ATAGTGTGAA | 60 |
| CCAGCTCTTT | GAAGAAGGCC | AGACTAAGGT | GTGGCCAGAA | GGTTCGTTAG | AAGAGACAGT | 120 |
| GCAAAACGCG | ATCAAGTCAT | GGGAGATGGA | GTTCTCACAT | AAGATCCGTT | TACAGGACTT | 180 |
| CAAGACTATA | AACCCTGAGA | AGTTTAAGCT | CTTTTGTCAA | TGGGAGAGAA | GGTTT | 235 |

(2) INFORMATION FOR SEQ ID NO:14:

(i) SEQUENCE CHARACTERISTICS:
    (A) LENGTH: 177 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:14:

| | | | | | |
|---|---|---|---|---|---|
| GGTGAATCTT | TCGAGGTTGA | GGAGGCGGTG | GCTCTCGAGT | CACAAACCAT | AGCGCATATG | 60 |
| GTTGAAGACG | ACTGCGTNAN | CAACGGAGTC | CCTCTTCCTA | ACGTCACGAG | CAAGATCCTN | 120 |
| GCCAAGGTGA | TCGAGTATTG | CAAGAGGCAC | GTCGAGGCTG | CTGCCTNTAA | AGGCCGA | 177 |

(2) INFORMATION FOR SEQ ID NO:15:

(i) SEQUENCE CHARACTERISTICS:
    (A) LENGTH: 247 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:15:

| | | | | | |
|---|---|---|---|---|---|
| TCGTTTGCTC | GAAGATCCGC | TGCTTGATCT | GCTCGCCACA | CGCTATNGGA | GAGGNAANGG | 60 |
| TTAGGGTTAC | TNATTTTCCG | TCGAGTAGTC | TNACNNAAAA | CTGCAACGGC | TTACAACTTT | 120 |
| GATCCGCCAT | CGATTTTCGA | TTCTAAAGCT | TGGACGAAGN | AGAAGNANAA | AGTTCGATTC | 180 |
| GATTTCTGGA | GAGAAATTGG | GGGAAAGTTT | AAAAACGGAT | CCCTAAGGTA | GTCTGAGTCT | 240 |
| CTCTCTC | | | | | | 247 |

What is claimed is:

1. An isolated DNA molecule having the following sequence:
   (a) a DNA sequence encoding a plant-glutamate receptor containing a glutamate binding domain having the amino acid sequence of FIG. 6 (SEQ ID NO:1);
   (b) a DNA sequence encoding a plant glutamate receptor containing an amino acid sequence shown in FIG. 7A (Seq. ID. No:8), or FIG. 7B (Seq. ID. No:12);
   (c) a DNA sequence encoding a plant glutamate receptor and containing one of the nucleotide sequences shown in FIG. 7C (SEQ ID NOS:13–15);
   (d) a DNA sequence that hybridizes under stringent conditions to the complement of the coding sequence of part (a) or (b) or (c) and encodes a plant protein having glutamate receptor activity; or
   (e) a DNA sequence that hybridizes under stringent conditions to the coding sequence of part (a) or (b) or (c), wherein the plant protein encoded by the coding strand of the hybridizing DNA has glutamate receptor activity.

2. A recombinant DNA vector containing the DNA sequence of claim 1.

3. The recombinant DNA vector of claim 2, in which the DNA sequence is operatively associated with a regulatory sequence that controls gene expression in a host.

4. An engineered host cell that contains the DNA of claim 1.

5. An engineered host cell that contains the DNA of claim 1 operatively associated with a regulatory sequence that controls gene expression so that the DNA sequence of claim 1 is expressed by the host cell.

6. The engineered host cell of claim 4 or 5 in which the host cell is a continuous cell line.

7. A method for producing a plant glutamate receptor protein comprising:

(a) culturing the host cell of claim 5; and (b) recovering the plant glutamate receptor protein from the cell culture.

8. A transgenic plant in which the transgene comprises a DNA sequence of claim 1 operatively associated with a regulatory sequence that controls gene expression so that the DNA sequence of claim 1 is expressed by the transgenic plant.

* * * * *